(12) United States Patent
Strobel et al.

(10) Patent No.: US 7,186,735 B2
(45) Date of Patent: Mar. 6, 2007

(54) ACYLATED ARYLCYCLOALKYLAMINES AND THEIR USE AS PHARMACEUTICALS

(75) Inventors: Hartmut Strobel, Liederbach (DE); Paulus Wohlfart, Bensheim (DE); Peter Below, Frankfurt (DE)

(73) Assignee: Sanofi-Aventis Deutschland GmbH, Frankfurt (DE)

( * ) Notice: Subject to any disclaimer, the term of this patent is extended or adjusted under 35 U.S.C. 154(b) by 301 days.

(21) Appl. No.: 10/636,001

(22) Filed: Aug. 7, 2003

(65) Prior Publication Data

US 2004/0082628 A1     Apr. 29, 2004

Related U.S. Application Data

(60) Provisional application No. 60/432,312, filed on Dec. 10, 2002.

(30) Foreign Application Priority Data

Aug. 7, 2002   (EP)   .................................. 02017587

(51) Int. Cl.
| | |
|---|---|
| C07D 401/06 | (2006.01) |
| C07D 277/24 | (2006.01) |
| C07D 263/32 | (2006.01) |
| C07D 409/06 | (2006.01) |
| C07D 207/333 | (2006.01) |
| A61K 31/4439 | (2006.01) |
| A61K 31/426 | (2006.01) |
| A61K 31/421 | (2006.01) |
| A61K 31/40 | (2006.01) |
| A61K 31/4025 | (2006.01) |

(52) U.S. Cl. ...................... 514/343; 514/365; 514/374; 514/422; 514/423; 546/279.1; 548/200; 548/236; 548/527; 548/537

(58) Field of Classification Search ................ 514/343, 514/365, 374, 422; 548/200, 236, 527, 537, 548/524; 546/279.1
See application file for complete search history.

(56) References Cited

U.S. PATENT DOCUMENTS

| | | | | | |
|---|---|---|---|---|---|
| 3,192,229 | A | * | 6/1965 | Biel | ........................... 548/537 |
| 4,614,810 | A | | 9/1986 | Georglev et al. | |
| 5,849,766 | A | * | 12/1998 | Jakubowski et al. | ........ 514/340 |
| 5,945,431 | A | | 8/1999 | Jin et al. | |
| 6,008,240 | A | | 12/1999 | Phillips et al. | |
| 6,617,359 | B2 | | 9/2003 | Wohlfart et al. | |
| 6,759,412 | B2 | | 7/2004 | Strobel | |
| 6,812,253 | B2 | | 11/2004 | Wohlfart et al. | |
| 6,949,556 | B2 | | 9/2005 | Strobel | |
| 2003/0055093 | A1 | | 3/2003 | Strobel | |
| 2004/0092513 | A1 | | 5/2004 | Strobel | |
| 2004/0110808 | A1 | | 6/2004 | Strobel | |
| 2004/0225013 | A1 | | 11/2004 | Strobel | |
| 2005/0049237 | A1 | * | 3/2005 | Atkinson et al. | ........ 514/210.2 |
| 2005/0054729 | A1 | | 3/2005 | Strobel | |
| 2005/0101599 | A1 | | 5/2005 | Zeiher | |

FOREIGN PATENT DOCUMENTS

| | | |
|---|---|---|
| EP | 0237028 A1 | 9/1987 |
| WO | WO98/36749 A1 | 8/1998 |
| WO | WO99/47153 A2 | 9/1999 |
| WO | WO00/03746 A2 | 1/2000 |
| WO | WO02/20530 A1 | 3/2002 |
| WO | WO 02/064146 A1 | 8/2002 |
| WO | WO 02/064545 A1 | 8/2002 |
| WO | WO 02/064546 A2 | 8/2002 |
| WO | WO 02/064565 A1 | 8/2002 |
| WO | WO 2003037274 A2 * | 5/2003 |

OTHER PUBLICATIONS

Chang, et al. "Substituted Imidazoles and Glucagon Receptor Antagonists," Bioorg. and Med. Chem. Letts., (2001) pp. 2549-2553.*
Mateos-Careres et al. "Prior Asprin use in unstable angina patients with modified plasma inflammatory markers and endothelial nitric oxide synthase in neutorphils" European J. of Clinical Investigation (20020) 32, 895-900.*
Freedman et al. "Nitric Oxide and its relationship to thrombotic disorders" J. Thrombosis and Haemostasis, 1: 1183-1188 (2003).*
Mateos-Careres et al. European J. of Clinical Investigation (2002) 32, 895-900.*
Freedman et al. J. Thrombosis and Haemostasis, 1:1183-1188 (2003).*
Aggarwal, et al., Catalytic Cyclopropanation Of Alkenes Using Diazo Compounds Generated In Situ. A Novel Route To 2-Arylcyclopropylamines, Org. Letters, 2001, 3 (17) 2785-2788.
Brown, et al., Organoboranes For Synthesis 7. An Improved General Synthesis of Primary Amines From Alkenes via Hydroboration-Organoborane Chemistry, Terahedron, 1987, 43 (18), 4071-4078.
Coutts, et al., Neurochemical and Neuropharmacological Properties of 4-Fluorotranylcypromine, Cell. Mol. Neurobiol., 1987, 7 (3), 271-291.
Endres, et al., Stroke Protection By 3-hydroxy-3-methylglutaryl (HMG)-CoA Reductase Inhibitors Mediated By Endothelial Nitric Oxide Synthase, Proc. Natl. Acad. Sci. USA, 1998, 95, 8880-8885.
Li, et al., Activation Of Protein Kinase Cα and or ε Enhances Transcription of the Human Endothelial Nitric Oxide Synthase Gene, Mol. Pharmacol., 1998, 53, 630-637.
Moroi, et al., Interaction Of Genetic Deficiency Of Endothelial Nitric Oxide, Gender, and Pregnancy In Vascular Response To Injury In Mice, J. Clin. Invest., 1998, 101 (6), 1225-1232.

(Continued)

Primary Examiner—Kamal A. Saeed
Assistant Examiner—Nyeemah Grazier
(74) Attorney, Agent, or Firm—Julie Anne Knight; Jiang Lin

(57) ABSTRACT

The present invention relates to acylated arylcycloalkylamines, to pharmaceutical compositions comprising such compounds, to methods for the stimulation of the expression of endothelial NO synthase, and methods of treatment comprising administering such compounds.

7 Claims, No Drawings

OTHER PUBLICATIONS

Nakayama, et al., T-786-C Mutation in the 5'-Flanking Region Of The Endothelial Nitric Oxide Synthase Gene Is Associated With Coronary Spasm, Circulation, 1999, 99, 2864-2870.

Sessa, et al., Chronic Exercise In Dogs Increases Coronary Vascular Nitric Oxide Production And Endothelial Cell Nitric Oxide Synthase Gene Expression, Circ. Research, 1994, 74, 349-353.

Varenne, et al., Percutaneous Gene Therapy Using Recombinant Adenoviruses Encoding Human Herpes Simplex Virus Thymidine Kinase, Human PAI-1, and Human NOS3 in Balloon-Injured Porcine Coronary Arteries, Hum. Gene Ther. 2000, 11, 1329-1339.

Wiehl, et al., Synthese Und Absolute Konfiguration 2-Substituierter Cyclopentanamine, Chem. Ber. 1986, 119, 2668-2677.

* cited by examiner

ACYLATED ARYLCYCLOALKYLAMINES AND THEIR USE AS PHARMACEUTICALS

This application is entitled to the benefit of earlier filed U.S. Provisional Application No. 60/432,312, filed Dec. 10, 2002. The content of U.S. Provisional Application 60/432,312 is incorporated herein by reference.

FILED OF THE INVENTION

The present invention relates to acylated arylcycloalkylamines of the formula I,

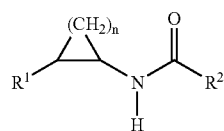

in which $R^1$, $R^2$ and n have the meanings indicated below. The compounds of formula I are valuable pharmaceutically active compounds which are useful in the treatment of various disease states including cardiovascular disorders such as atherosclerosis, thrombosis, coronary artery disease, hypertension and cardiac insufficiency. They upregulate the expression of the enzyme endothelial nitric oxide (NO) synthase and can be applied in conditions in which an increased expression of said enzyme or an increased NO level or the normalization of a decreased NO level is desired. The invention furthermore relates to processes for the preparation of compounds of the formula I, their use, in particular as active ingredients in pharmaceuticals, pharmaceutical preparations comprising them, methods of stimulating the expression of endothelial NO synthase, and methods of treatment comprising administering such compounds.

BACKGROUND OF THE INVENTION

Endothelial NO synthase (eNOS, NOS-III) belongs to a group of three isoenzymes which produce nitric oxide (NO) by oxidation of arginine. Endothelially released NO is of central importance in a number of key cardiovascular mechanisms. It has a vasodilating effect and inhibits the aggregation of platelets, the adhesion of leukocytes to the endothelium and the proliferation of intimal smooth muscle cells.

Endothelial NO synthase is subject to physiological and pathophysiological regulation both at the transcriptional and at the post-transcriptional level. Enzyme already present in the endothelium may undergo calcium-dependent and calcium-independent activation through phosphorylation of specific amino acids, but also by direct interactions with specific proteins. Stimulators of this, usually transient, NO release are, extracellular arginine, 17β-estrogen and the mechanical stimulus exerted on the luminal surface of the endothelium by the blood flow (shear stress). The latter additionally leads to regulation of eNOS at the transcriptional level. Thus, for example, Sessa et al. (Circ. Research 74 (1994) 349, the content of which is incorporated herein by reference) were able by means of exercise training and the increase in shear stress associated therewith to obtain a marked increase in eNOS.

Whether regulation at the post-transcriptional level is relevant in vivo, has not been unambiguously proven. Thus, for example, administration of a high arginine dose is followed by only a transient improvement in the endothelium-dependent vasorelaxation in patients with coronary heart disease.

On the other hand, the significance of the upregulation of the eNOS protein is scientifically accepted. Thus, there are findings which show that the protective properties of the HMG-CoA reductase inhibitor simvastatin can be attributed, besides to the lipid lowering effect, also in part to an increase in eNOS expression in vivo (Endres et al., Proc. Natl. Acad. Sci. USA 95 (1998) 8880, the content of which is incorporated herein by reference). It is additionally known that single point mutations in the 5'-flanking region of the eNOS gene ("eNOS promoter"), and the reduction in the rate of eNOS gene transcription associated therewith, in the Japanese population is associated with an increase in the risk of coronary spasms (Nakayama et al., Circulation 99 (1999) 2864, the content of which is incorporated herein by reference).

The current assumption therefore is that the transcriptional and post-transcriptional mechanisms of eNOS regulation are seriously disturbed in a large number of disorders, especially in cardiovascular disorders. Even in very early stages of a wide variety of cardiovascular disorders it is possible for a dysfunction of this type in the endothelium lining the blood vessels to lead to a deficiency of bioactive NO, which is manifested as the disorder progresses in the form of measurable pathophysiological and morphological changes. Thus, critical steps in early atherogenesis are speeded up by a decrease in endothelial NO release, such as, for example, the oxidation of low density lipoproteins, the recruitment and deposition of monocytes in the intima of vessels, and the proliferation of intimal cells. A consequence of atherogenesis is the formation of plaques on the inside of the blood vessels, which may in turn lead, through a diminution in the shear stress, to a further decrease in endothelial NO release and a further deterioration in the pathology. Since endothelial NO is also a vasodilator, a decrease thereof frequently also leads to hypertension, which may, as an independent risk factor, cause further organ damage.

The aim of a therapeutic approach to the treatment of these disorders must accordingly be to interrupt this chain of events by increasing the endothelial NO expression. Gene transfer experiments which lead in vitro to overexpression of NO synthase in previously damaged vessels are in fact able to counteract the described processes and are thus evidence of the correctness of this approach (Varenne et al., Hum. Gene Ther. 11 (2000) 1329, the content of which is incorporated herein by reference).

Some low molecular weight compounds which, in cell cultures, may lead to a direct effect on eNOS transcription and expression are disclosed in the literature. The statins which have already been mentioned are, however, the only substances for which it has been possible to date to show such an increase in eNOS in vivo as a side effect. But in view of the known range of side effects of this class of substances it is unclear how far this effect is present in a toxicologically unproblematic dose.

Liao et al. claim in WO 99/47153 and WO 00/03746, the content of each of which is incorporated herein by reference. the use of rhoGTPase inhibitors and agents which influence the organization of the actin cytoskeleton for increasing eNOS in endothelial cells and for the therapy of various disorders such as, for example, stroke or pulmonary hypertension without, however, indicating a specific way of achieving this.

WO 02/064146, WO 02/064545, WO 02/064565 and WO 02/064546, the content of each of which is incorporated herein by reference, disclose acylated, benzo-condensed cycloalkenylamines which upregulate eNOS expression in endothelial cells and are useful pharmaceutically active ingredients for the treatment of various diseases, but there is an ongoing need for further eNOS expression enhancers with a favorable property profile. The present invention satisfies this need by providing the compounds of the formula I and methods of using them.

SUMMARY OF THE INVENTION

The present invention relates to acylated arylcycloalkylamines of the formula I,

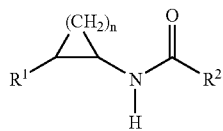

I in any of their stereoisomeric forms and mixtures thereof in any ratio, and the pharmaceutically acceptable salts thereof, wherein in the formula I:

$R^1$ is aryl or heteroaryl both of which are unsubstituted or substituted by one or more identical or different substituents selected from the group consisting of $C_1$–$C_6$-alkyl, halogen, $CF_3$, $C_1$–$C_6$-alkoxy, $C_1$–$C_6$-alkylmercapto, —CN, $COOR^{10}$, $CONR^{11}R^{12}$, $NR^{13}R^{14}$, $S(O)_m R^{15}$ and $S(O)_2 NR^{16}R^{17}$;

$R^2$ is aryl or heteroaryl both of which are unsubstituted or carry one or more identical or different substituents selected from the group consisting of:

halogens; —CN; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, $C_1$–$C_{10}$-alkylamino and di($C_1$–$C_{10}$-alkyl) amino, the substituents of which are selected from the group consisting of F, OH, $C_1$–$C_8$-alkoxy, aryloxy, $C_1$–$C_8$-alkylmercapto, $NH_2$, $C_1$–$C_8$-alkylamino and di($C_1$–$C_8$-alkyl)amino; $C_3$–$C_5$-alkandiyl; phenyl; heteroaryl; aryl-substituted or heteroaryl-substituted $C_1$–$C_4$-alkyl; $CF_3$; $NO_2$; OH; phenoxy; benzyloxy; ($C_1$–$C_{10}$-alkyl)-COO—; $S(O)_m R^{20}$; SH; phenylamino; benzylamino; ($C_1$–$C_{10}$-alkyl)-CONH—; ($C_1$–$C_{10}$-alkyl)-CO—N($C_1$–$C_4$-alkyl)-; phenyl-CONH—; phenyl-CO—N($C_1$–$C_4$-alkyl)-; heteroaryl-CONH—; heteroaryl-CO—N($C_1$–$C_4$-alkyl)-; ($C_1$–$C_{10}$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; C(NH)—$NH_2$; $SO_2NR^{24}R^{25}$; $R^{26}SO_2NH$—; $R^{27}SO_2N(C_1$–$C_6$-alkyl)-; and a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogens, $C_1$–$C_3$-alkyl, $C_1$–$C_3$-alkoxy, OH, oxo and $CF_3$, where said heterocycle can optionally be condensed to the said aryl group or heteroaryl group representing $R^2$; wherein all aryl, heteroaryl, phenyl, aryl-containing, heteroaryl-containing and phenyl-containing groups, which are optionally present in the said substituents of the said aryl group or heteroaryl group representing $R^2$, can be substituted by one or more substituents selected from the group consisting of halogens, —CN, $C_1$–$C_3$-alkyl, OH, $C_1$–$C_3$-alkoxy and $CF_3$;

$R^{10}$ is H, $C_1$–$C_6$-alkyl or benzyl wherein the phenyl group can be substituted by one or more identical or different substituents from the group consisting of halogens, —CN, $C_1$–$C_3$-alkyl, $C_1$–$C_3$-alkoxy and $CF_3$;

$R^{11}$ is selected from the group consisting of:

H; $C_1$–$C_6$-alkyl which can be substituted by phenyl; phenyl; indanyl; and heteroaryl; wherein each of the aromatic groups is unsubstituted or carries one or more identical or different substituents from the group consisting of halogens, —CN, $C_1$–$C_3$-alkyl, $C_1$–$C_3$-alkoxy and $CF_3$;

$R^{12}$ is H or $C_1$–$C_6$-alkyl;

$R^{13}$ is selected from the group consisting of:

H; $C_1$–$C_6$-alkyl; and unsubstituted and substituted phenyl, benzyl, heteroaryl, phenyl-CO—, and heteroaryl-CO—, the substituents of which are selected from the group consisting of halogens, —CN, $C_1$–$C_3$-alkyl, $C_1$–$C_3$-alkoxy and $CF_3$, wherein one or more of these substituents can be present;

$R^{14}$ is H or $C_1$–$C_6$-alkyl;

$R^{15}$ is selected from the group consisting of:

$C_1$–$C_6$-alkyl; $CF_3$; and substituted and unsubstituted phenyl and heteroaryl, the substituents of which are selected from the group consisting of halogens, —CN, $C_1$–$C_3$-alkyl, $C_1$–$C_3$-alkoxy and $CF_3$, wherein one or more of these substituents can be present;

$R^{16}$, independently from $R^{11}$, is defined as $R^{11}$;

$R^{17}$, independently from $R^{12}$, is defined as $R^{12}$;

$R^{20}$ is selected from the group consisting of:

$C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino; $CF_3$; and substituted and unsubstituted phenyl and heteroaryl, the substituents of which are selected from the group consisting of halogens, —CN, $C_1$–$C_3$-alkyl, $C_1$–$C_3$-alkoxy and $CF_3$, wherein one or more of these substitutents can be present;

$R^{21}$ is selected from the group consisting of:

H; $C_1$–$C_{10}$-alkyl which can be substituted by one or more substituents selected from the group consisting of F, $C_1$–$C_8$-alkoxy and di($C_1$–$C_8$-alkyl)amino; aryl-($C_1$–$C_4$-alkyl)- and heteroaryl-($C_1$–$C_4$-alkyl)- both of which can be substituted by one or more substituents selected from the group consisting of halogens, $C_1$–$C_4$-alkyl, $C_1$–$C_4$-alkoxy and di($C_1$–$C_6$-alkyl)amino;

$R^{22}$ is selected from the group consisting of:

H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl; and heteroaryl; wherein each of the aromatic groups can be unsubstituted or carry one or more substituents selected from the group consisting of halogens, —CN, $C_1$–$C_3$-alkyl, $C_1$–$C_3$-alkoxy and $CF_3$;

$R^{23}$ is H or $C_1$–$C_{10}$-alkyl;

$R^{24}$, independently from $R^{22}$, is defined as $R^{22}$;

$R^{25}$, independently from $R^{23}$, is defined as $R^{23}$;

$R^{26}$, independently from $R^{20}$, is defined as $R^{20}$;

$R^{27}$, independently from $R^{20}$, is defined as $R^{20}$;

heteroaryl is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

m is 0, 1 or 2;

n is 1, 2, 3 or 4;

with the proviso that, if $R^1$ is unsubstituted phenyl, $R^2$ cannot be unsubstituted phenyl, 4-bromophenyl, 3-methoxyphenyl, chlorosubstituted 4H-thieno[3,2-b]pyrrol-5-yl, unsubstituted thienyl, naphthyridinyl, unsubstituted pyridinyl, 3-hydroxy-4-methoxypyridin-2-yl, 2,6-dichloropyridin-4-yl or 3,4,5-trimethoxyphenyl.

If groups or substituents in the compounds of the formula I such as, for example, aryl, heteroaryl, alkyl etc., can be present several times, they all independently from each other have the meanings indicated and can hence, in each individual case, be identical with or different from each other. As an example the di($C_1$–$C_{10}$-alkyl)amino group may be mentioned in which the alkyl substituents can be identical or different. When a group in the compounds of the formula I can be at least monosubstituted, or when it carries one or more substituents, it can be substituted, for example, by one, two, three, four or five substituents. When a group is substituted by two or more substituents, the substituents can be identical or different from each other.

When a substituent group is defined in terms of another substituent group, and those are indicated to be independent of each other, for example, as in the phrases, "$R_{16}$, independently from $R^{11}$," is defined as $R^{11}$, this means that they take on the same nature and range of values, but that they individually may be the same or different.

Alkyl, alkenyl and alkynyl residues can be linear or branched, acyclic or cyclic. This also applies when they are part of other groups, for example alkoxy groups, alkoxycarbonyl groups or substituted amino groups, or when they are substituted.

Examples of alkyl groups are methyl, ethyl, propyl, butyl, pentyl, hexyl, heptyl, octyl, nonyl, decyl, the n-isomers of these residues, isopropyl, isobutyl, isopentyl, sec-butyl, tert-butyl, neopentyl, 3,3-dimethylbutyl. The term alkyl here also expressly includes cycloalkyl groups and cycloalkyl-alkyl- groups (i. e., alkyl substituted by cycloalkyl) which groups contain at least three carbon atoms. Examples of such cycloalkyl residues are cyclopropyl, cyclobutyl, cyclopentyl, cyclohexyl, cycloheptyl and cyclooctyl. All cycloalkyl groups can be substituted by one or more identical or different $C_1$–$C_4$-alkyl residues, in particular by methyl. Examples of substituted cycloalkyl residues are 4-methylcyclohexyl, 4-tert-butylcyclohexyl or 2,3-dimethylcyclopentyl. Furthermore, unless stated otherwise, the term alkyl here also includes unsubstituted alkyl residues as well as alkyl residues which are substituted by one or more, for example 1, 2, 3 or 4, identical or different residues, for example aryl groups. In substituted alkyl residues, for example arylalkyl-, hydroxyalkyl- such as hydroxy-($C_1$–$C_3$)-alkyl- or alkoxyalkyl- such as $C_1$–$C_4$-alkyl-O—($C_1$–$C_3$)-alkyl-, the substituents can be present in any desired position.

Examples of alkenyl and alkynyl groups are vinyl, 1-propenyl, 2-propenyl (i.e. allyl), 2-butenyl, 2-methyl-2-propenyl, 3-methyl-2-butenyl, ethynyl, 2-propynyl (i.e. propargyl), 2-butynyl or 3-butynyl. The term alkenyl here also expressly includes cycloalkenyl groups and cycloalkenyl-alkyl- groups (i.e. alkyl substituted by cycloalkenyl) which groups contain at least three carbon atoms. Examples of cycloalkenyl residues are cyclopentenyl, cyclohexenyl, cycloheptenyl and cyclooctenyl. All cycloalkenyl groups can be substituted by one or more identical or different $C_1$–$C_4$-alkyl residues, in particular by methyl. Furthermore, unless stated otherwise, the term alkenyl and alkynyl here also includes unsubstituted alkenyl and alkynyl residues as well as alkenyl and alkynyl residues which are substituted by one or more, for example 1, 2, 3 or 4, identical or different residues, for example aryl groups. In substituted alkenyl and alkynyl residues, for example arylalkenyl-, hydroxyalkenyl- such as hydroxy-($C_2$–$C_3$)-alkenyl- or alkoxyalkenyl- such as $C_1$–$C_3$-alkyl-O—($C_2$–$C_4$-alkenyl)-, the substituents can be present in any desired position.

Examples of $C_3$–$C_5$-alkandiyl are —$CH_2CH_2CH_2$—, —$CH_2$—$CH(CH_3)$—, —$CH_2CH_2CH_2CH_2$— and —$CH_2CH_2CH_2CH_2CH_2$— groups.

If not stated otherwise, the above-mentioned phenyl residues, naphthyl and indanyl residues and heterocyclic residues (including heteroaryl residues) can be unsubstituted or can carry one or more, for example 1, 2, 3 or 4, of the substituents indicated in the above definition which substituents can be present in any desired position. If in compounds of the formula I nitro groups are present as substituents, in a preferred embodiment of the invention in total only up to two nitro groups are present in the molecule. In monosubstituted phenyl residues the substituent can be in the 2-position, the 3-position or the 4-position, in disubstituted phenyl residues the substituents can be in 2,3-position, 2,4-position, 2,5-position, 2,6-position, 3,4-position or 3,5-position. In trisubstituted phenyl residues the substituents can be in 2,3,4-position, 2,3,5-position, 2,3,6-position, 2,4,5-position, 2,4,6-position or 3,4,5-position. In fourfold substituted phenyl residues, the substituents can be in the 2,3,4,5-position, the 2,3,4,6-position, or the 2,3,5,6-position. Tolyl (=methylphenyl) can be 2-tolyl, 3-tolyl or 4-tolyl. Naphthyl can be 1-naphthyl or 2-naphthyl. In monosubstituted 1-naphthyl residues the substituent can be in the 2-position, the 3-position, the 4-position, the 5-position, the 6-position, the 7-position or the 8-position, in monosubstituted 2-naphthyl residues in the 1-position, the 3-position, the 4-position, the 5-position, the 6-position, the 7-position or the 8-position. In higher substituted naphthyl residues, for example 1-naphthyl residues or 2-naphthyl residues which carry two or three substituents, the substituents can be present in any desired positions. Indanyl residues include indan-1-yl residues and indan-2-yl residues which can be unsubstituted or carry one or more of the substituents indicated. In case the indanyl residues are substituted, the substituent or substituents can be present in any of the positions possible.

Unless stated otherwise, heteroaryl residues and heterocyclic residues are preferably derived from heterocycles which contain 1, 2, 3 or 4 heteroatoms which can be identical or different; more preferably they are derived from heterocycles which contain 1, 2 or 3, in particular 1 or 2, heteroatoms which can be identical or different. Unless stated otherwise, the heterocycles can be monocyclic or polycyclic, for example monocyclic, bicyclic or tricyclic. Preferably they are monocyclic or bicyclic. The number of ring members preferably is 5, 6, 8, 9 or 10. The individual rings preferably are 5-membered rings, 6-membered rings or 7-membered rings. Examples of monocyclic and bicyclic heterocyclic systems from which residues occurring in the compounds of the formula I can be derived, are pyrrole, furan, thiophene, imidazole, pyrazole, 1,2,3-triazole, 1,2,4-triazole, 1,3-dioxole, 1,3-oxazole (=oxazole), 1,2-oxazole (=isoxazole), 1,3-thiazole (=thiazole), 1,2-thiazole (=isothiazole), tetrazole, pyridine, pyridazine, pyrimidine, pyrazine, pyran, thiopyran, 1,4-dioxine, 1,2-oxazine, 1,3-oxazine, 1,4-oxazine, 1,2-thiazine, 1,3-thiazine, 1,4-thiazine, 1,2,3-triazine, 1,2,4-triazine, 1,3,5-triazine, 1,2,4,5-tetrazine, azepine, 1,2-diazepine, 1,3-diazepine, 1,4-diazepine, 1,3-oxazepine, 1,3-thiazepine, indole, benzothiophene, benzofuran, benzothiazole, benzoxazole, benzimidazole, benzodioxole, quinoline, isoquinoline, cinnoline, quinazoline, quinoxaline, phthalazine, thienothiophenes, 1,8-naphthyridine and other naphthyridines, pteridin, or phenothiazine, each of them in saturated form (perhydro form) or in partially unsaturated form (for example in the dihydro form or the tetrahydro form) or in maximally unsaturated form or aromatic form, provided that the respective forms are known and stable. The term "aryl" and the term "heteroaryl" as used herein comprise bicyclic residues in which both cycles are aromatic as well as bicyclic residues in which only one cycle is aromatic. Suitable heterocycles include, for example, the saturated heterocycles pyrrolidine, piperidine, piperazine, morpholine and thiomorpholine. The degree of saturation of heterocyclic groups is indicated in their individual definitions. Unsaturated heterocycles can contain, for example, 1, 2 or 3, double bonds within the ring system. 5-membered rings and 6-membered rings can in particular also be aromatic.

Residues derived from the mentioned heterocycles can be attached via any suitable carbon atom. Residues derived from nitrogen heterocycles which can carry a hydrogen atom or a substituent on a ring nitrogen atom, such as pyrrole, imidazole, pyrrolidine, morpholine or piperazine residues, can also be attached via a ring nitrogen atom, in particular if the respective heterocyclic residue is attached to a carbon atom. For example, a thienyl residue can be present as 2-thienyl residue or 3-thienyl residue, a furyl residue as 2-furyl residue or 3-furyl residue, a pyridinyl residue as 2-pyridinyl residue, 3-pyridinyl residue or 4-pyridinyl residue, a piperidinyl residue as 1-piperidinyl residue (=piperidino residue), 2-piperidinyl residue, 3-piperidinyl residue or 4-piperidinyl residue, a (thio)morpholinyl residue as 2-(thio)morpholinyl residue, 3-(thio)morpholinyl residue or 4-(thio)morpholinyl residue (=thiomorpholino residue). A residue derived from 1,3-thiazole or imidazole which is attached via a carbon atom can be attached via the 2-position, the 4-position or the 5-position.

In case a heterocyclic groups is substituted, it can carry one or more, for example 1, 2, 3 or 4, identical or different substituents. Substituents in heterocycles can be present in any desired positions, for example in a 2-thienyl residue or 2-furyl residue in the 3-position and/or in the 4-position and/or in the 5-position, in a 3-thienyl residue or 3-furyl residue in the 2-position and/or in the 4-position and/or in the 5-position, in a 2-pyridinyl residue in the 3-position and/or in the 4-position and/or in the 5-position and/or in the 6-position, in a 3-pyridinyl residue in the 2-position and/or in the 4-position and/or in the 5-position and/or in the 6-position, in a 4-pyridinyl residue in the 2-position and/or in the 3-position and/or in the 5-position and/or in the 6-position. Suitable nitrogen heterocycles can also be present as N-oxides or as quarternary salts containing a counterion which is derived from a pharmaceutically acceptable acid. Pyridine moieties, for example, can thus be present as pyridine-N-oxides.

Halogen is fluorine, chlorine, bromine or iodine, preferably fluorine or chlorine.

The present invention includes all stereoisomeric forms of the compounds of the formula I. Centers of asymmetry that are present in the compounds of formula I all independently from one another can have S configuration or R configuration. The invention includes all possible enantiomers and diastereomers and mixtures of two or more stereoisomers, for example mixtures of enantiomers and/or diastereomers, in all ratios. Thus, compounds of the present invention which can exist as enantiomers can be present in enantiomerically pure form, both as levorotatory and as dextrorotatory antipodes, in the form of racemates and in the form of mixtures of the two enantiomers in all ratios. As regards cis/trans isomerism which also occurs, for example, on the cycloalkyl ring in formula I with respect to the relative position of the residues $R^1$ and $R^2$—CO—NH—, the invention includes both the cis form and the trans form as well as mixtures of these forms in all ratios. All these forms are a subject of the present invention. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at the stage of the compounds of the formula I or at the stage of an intermediate during the synthesis or at the stage of a starting compound. The present invention also includes all tautomeric forms of the compounds of formula I.

In case the compounds of formula I contain one or more acidic or basic groups, the invention also comprises their corresponding pharmaceutically or toxicologically acceptable salts, in particular their pharmaceutically utilizable salts. Thus, the compounds of the formula I which contain acidic groups can be present on these groups and can be used according to the invention, for example, as alkali metal salts, alkaline earth metal salts or as ammonium salts. Examples of such salts include sodium salts, potassium salts, calcium salts, magnesium salts or salts with ammonia or organic amines such as, for example, ethylamine, ethanolamine, triethanolamine or amino acids. Compounds of the formula I which contain one or more basic groups, i.e. groups which can be protonated, can be present and can be used according to the invention in the form of their addition salts with inorganic or organic acids. Examples of suitable acids include hydrogen chloride, hydrogen bromide, phosphoric acid, sulfuric acid, nitric acid, methanesulfonic acid, p-toluenesulfonic acid, naphthalenedisulfonic acids, oxalic acid, acetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfamic acid, phenylpropionic acid, gluconic acid, ascorbic acid, isonicotinic acid, citric acid, adipic acid, and other acids known to the person skilled in the art. If the compounds of the formula I simultaneously contain acidic and basic groups in the molecule, the invention also includes, in addition to the salt forms mentioned, inner salts or betaines (zwitterions). The salts of the compounds of the formula I can be obtained by customary methods which are known to the person skilled in the art like, for example, by contacting the compound of the formula I with an organic or inorganic acid or base in a solvent or diluent, or by anion exchange or cation exchange from another salts. The present invention also includes all salts of the compounds of the formula I which, owing to low physiological compatibility, are not directly suitable for use in pharmaceuticals but which can be used, for example, as intermediates for chemical reactions or for the preparation of pharmaceutically acceptable salts.

The present invention furthermore includes all solvates of compounds of the formula I, for example hydrates and adducts with alcohols, active metabolites of the compounds of the formula I, and also derivatives and prodrugs of the compounds of the formula I which contain physiologically tolerable and cleavable groups, for example esters, amides and compounds in which the N—H group depicted in formula I is replaced with an N-alkyl group, such as N-methyl, or with an N-acyl group, such as N-acetyl or N-argininyl, including pharmaceutically acceptable salts formed on functional groups present in the N-acyl group.

In preferred embodiments of the present invention, one or more of the structural moieties in the compounds of formula I, including the number n, the groups $R^1$ and $R^2$ and the other groups present in the compounds of formula I, independently from each other have the following preferred meanings, more preferred meanings, even more preferred meanings or most preferred meanings.

$R^1$ is preferably phenyl or monocyclic 5-membered or 6-membered heteroaryl both which are unsubstituted or substituted by one or more identical or different substituents, for example substituents selected from the group consisting of $C_1$–$C_4$-alkyl, $C_1$–$C_4$-alkoxy, $CF_3$, halogens and $C_1$–$C_4$-alkyl-S(O)$_m$—. More preferably $R^1$ is phenyl, thienyl or pyridinyl, in particular phenyl, all of which are unsubstituted or substituted by one or more identical or different substituents selected from the group consisting of $C_1$–$C_3$-alkyl, $CF_3$ and halogens.

$R^2$ is preferably aryl or heteroaryl both of which are unsubstituted or carry one or more identical or different substituents selected from the group consisting of: halogens; —CN; $NH_2$; unsubstituted and at least monosubstituted $C_1$–$C_8$-alkyl, $C_2$–$C_8$-alkenyl, $C_2$–$C_8$-alkynyl, $C_1$–$C_8$-alkoxy, $C_1$–$C_8$-alkylamino and di($C_1$–$C_8$-alkyl)amino, the substituents of which are selected from the group consisting of F, OH, $C_1$–$C_6$-alkoxy, phenoxy, $C_1$–$C_6$-alkylmercapto, $NH_2$, $C_1$–$C_6$-alkylamino and di($C_1$–$C_6$-alkyl)amino; $C_3$–$C_5$-alkandlyl; phenyl; heteroaryl; phenyl-substituted or heteroaryl-substituted $C_1$–$C_2$-alkyl; $CF_3$; OH; phenoxy; benzyloxy; ($C_1$–$C_6$-alkyl)-COO; S(O)$_m$—($C_1$–$C_6$)-alkyl which can optionally be substituted by OH or $C_1$–$C_6$-alkoxy; S(O)$_m$-phenyl; S(O)$_m$-heteroaryl; SH; phenylamino; benzylamino; ($C_1$–$C_6$-alkyl)-CONH—; ($C_1$–$C_6$-alkyl)-CON($C_1$–$C_4$-alkyl)-; phenyl-CONH—; phenyl-CON($C_1$–$C_4$-alkyl)-; heteroaryl-CONH—; heteroaryl-CON($C_1$–$C_4$-alkyl)-; ($C_1$–$C_6$-alkyl)-CO—; phenyl-CO—; heteroaryl-CO—; $CF_3$—CO—; —OCH$_2$O—; —OCF$_2$O—; —OCH$_2$CH$_2$O—; —CH$_2$CH$_2$O—; COO($C_1$–$C_6$-alkyl); —CONH$_2$; —CONH($C_1$–$C_6$-alkyl); —CON(di($C_1$–$C_6$-alkyl)); C(NH)—NH$_2$; —SO$_2$NH$_2$; —SO$_2$NH($C_1$–$C_6$-alkyl); —SO$_2$NH(phenyl); —SO$_2$N(di($C_1$–$C_6$-alkyl)); $C_1$–$C_6$-alkyl-SO$_2$NH—; ($C_1$–$C_6$-alkyl)-SO$_2$N($C_1$–$C_6$-alkyl)-; phenyl-SO$_2$NH—; phenyl-SO$_2$N($C_1$–$C_6$-alkyl)-; heteroaryl-SO$_2$NH—; heteroaryl-SO$_2$N($C_1$–$C_6$-alkyl)-; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogens, $C_1$–$C_3$-alkyl, $C_1$–$C_3$-alkoxy, OH, oxo and $CF_3$, where said heterocycle can optionally be condensed to the said aryl group or heteroaryl group representing $R^2$; wherein all heteroaryl, phenyl, heteroaryl-containing and phenyl-containing groups, which are optionally present in the said substituents of the said aryl group or heteroaryl group representing $R^2$, can be substituted by one or more substituents selected from the group consisting of halogens, —CN, $C_1$–$C_3$-alkyl, OH, $C_1$–$C_3$-alkoxy, and $CF_3$.

$R^2$ is more preferably phenyl or heteroaryl both of which are unsubstituted or carry one or more identical or different substituents selected from the group consisting of: halogens; —CN; $NH_2$; unsubstituted and at least monosubstituted $C_1$–$C_6$-alkyl, $C_2$–$C_6$-alkenyl, $C_2$–$C_6$-alkynyl, $C_1$–$C_3$-alkoxy, $C_1$–$C_4$-alkylamino and di($C_1$–$C_4$-alkyl)amino, the substituents of which are selected from the group consisting of F, $C_1$–$C_3$-alkoxy, $C_1$–$C_3$-alkylmercapto and $NH_2$; $C_3$–$C_5$-alkandiyl; phenyl; heteroaryl; phenyl-substituted or heteroaryl-substituted $C_1$–$C_2$-alkyl; $CF_3$; OH; ($C_1$–$C_4$-alkyl)-COO; S(O)$_m$—($C_1$–$C_4$)-alkyl; ($C_1$–$C_4$-alkyl)-CONH—; ($C_1$–$C_4$-alkyl)-CON($C_1$–$C_4$-alkyl)-; ($C_1$–$C_4$-alkyl)-CO—; phenyl-CO—; heteroaryl-CO—; $CF_3$—CO—; —OCH$_2$O—; —OCF$_2$O—; —OCH$_2$CH$_2$O—; —CH$_2$CH$_2$O—; COO($C_1$–$C_6$-alkyl); —CONH$_2$; —CONH ($C_1$–$C_4$-alkyl); —CON(di($C_1$–$C_4$-alkyl)); C(NH)NH$_2$; —SO$_2$NH$_2$; —SO$_2$NH($C_1$–$C_4$-alkyl); —SO$_2$NH(phenyl); —SO$_2$N(di($C_1$–$C_4$-alkyl)); ($C_1$–$C_4$-alkyl)-SO$_2$NH—; ($C_1$–$C_4$-alkyl)-SO$_2$N($C_1$–$C_4$-alkyl)-; and a residue of a saturated or at least monounsaturated aliphatic, mononuclear 5-membered to 7-membered heterocycle containing 1, 2 or 3 heteroatoms selected from the group consisting of N, O and S, which heterocycle can be substituted by one or more substituents selected from the group consisting of halogens, $C_1$–$C_3$-alkyl, $C_1$–$C_3$-alkoxy, OH, oxo and $CF_3$, where said heterocycle can optionally be condensed to the said phenyl group or heteroaryl group representing $R^2$; wherein all heteroaryl, phenyl, heteroaryl-containing and phenyl-containing groups, which are optionally present in the said substituents of the said phenyl group or heteroaryl group representing $R^2$, can be substituted by one or more substituents selected from the group consisting of halogens, —CN, $C_1$–$C_3$-alkyl, OH, $C_1$–$C_3$-alkoxy, and $CF_3$.

$R^2$ is even more preferably phenyl or heteroaryl both of which are unsubstituted or carry one or more identical or different substituents selected from the group consisting of: F; Cl; Br; $C_1$–$C_3$-alkyl; $C_1$–$C_3$-alkoxymethyl; 2-amino-3,3,3-trifluoropropyl-; $CF_3$; $C_3$–$C_5$-alkandiyl; phenyl; heteroaryl; benzyl; heteroaryl-methyl-; OH; $C_1$–$C_3$-alkoxy; phenoxy; trifluoromethoxy; 2,2,2-trifluoroethoxy; ($C_1$–$C_4$-alkyl)-COO; $C_1$–$C_3$-alkylmercapto; phenylmercapto; $C_1$–$C_3$-alkylsulfonyl; phenylsulfonyl; $NH_2$; $C_1$–$C_4$-alkylamino; di($C_1$–$C_4$-alkyl)amino; ($C_1$–$C_3$-alkyl)-CONH—; ($C_1$–$C_3$-alkyl)-SO$_2$NH—; ($C_1$–$C_3$-alkyl)-CO—; phenyl-CO—; —OCH$_2$O—; —OCF$_2$O—; —CH$_2$CH$_2$O—; COO ($C_1$–$C_4$-alkyl); —CONH$_2$; —CONH($C_1$–$C_4$-alkyl); —CON (di($C_1$–$C_4$-alkyl)); —CN; —SO$_2$NH$_2$; —SO$_2$NH($C_1$–$C_4$-alkyl); —SO$_2$N(di($C_1$–$C_4$-alkyl)); pyrrolidinyl; piperidinyl; morpholinyl and thiomorpholinyl; wherein all heteroaryl, phenyl, heteroaryl-containing and phenyl-containing groups, which are optionally present in the said substituents of the said phenyl group or heteroaryl group representing $R^2$, can be substituted by one or more substituents selected from the group consisting of halogens, —CN, $C_1$–$C_3$-alkyl, OH, $C_1$–$C_3$-alkoxy, and $CF_3$.

$R^2$ is most preferably selected from the group consisting of 4-fluorophenyl, 4-chlorophenyl, 4-bromophenyl, 4-($C_1$–$C_3$-alkoxy)-phenyl, 4-trifluoromethoxyphenyl, 2-bromo-4-fluorophenyl, 2-chloro-4-fluorophenyl, 3,4-dimethylphenyl, 2,4-dimethylphenyl, 4-chloro-2-methylphenyl, 2-hydroxy-4-methylphenyl, 2-hydroxy-4-ethoxyphenyl, 2-methoxy-4-methylphenyl, 4-phenoxyphenyl, 3-fluoro-4-methylphenyl, benzo[1,3]dioxol-5-yl, 2,2-difluoro-benzo[1,3]dioxol-5-yl, 2,3-dihydrobenzofuran-5-yl, 1-(4-chlorophenyl)-5-trifluoromethyl-1H-pyrazol-4-yl, 1-(4-fluorophenyl)-3,5-dimethyl-1H-pyrazol-4-yl, 1H-benzotriazol-5-yl, 1H-indol-4-yl, 1H-indol-6-yl, 1-isopropyl-2-trifluoromethyl-1H-benzimidazol-5-yl, 1-methyl-3-oxo-1,2,3,4-tetrahydro-quinoxalin-6-yl, 1-phenyl-5-trifluoromethyl-1H-pyrazol-4-yl, 2-(2-hydroxypyridin-4-yl)-1H-benzimidazol-5-yl, 2-(4-cyanophenyl)-1H-benzimidazol-5-yl, 2,4-dimethyloxazol-5-yl, 2,4-dimethylpyrimidin-5-yl, 2,4-dimethylthiazol-5-yl, 2,5-dimethyl-1H-pyrrol-3-yl, 2,5- dimethyl-1-phenyl-1H-pyrrol-3-yl, 2,5-dimethyl-1-(pyridin-4-ylmethyl)-1H-pyrrol-3-yl, 2,5-dimethyl-2H-pyrazol-3-yl, 2,6-dichloropyridin-3-yl, 2,6-dimethoxypyridin-3-yl, 2,6-dimethylpyridin-3-yl, 2-amino-4,6-dimethylpyridin-3-yl, 2-amino-6-chloropyridin-3-yl, 2-aminopyridin-3-yl, 2-chloro-6-methylpyridin-3-yl, 2-chloropyridin-4-yl, 2-cyclopropyl-4-methylthiazol-5-yl, 2-dimethylamino-4-methylthiazol-5-yl, 2-dimethylaminopyridin-4-yl, 2-ethyl-5-methyl-2H-pyrazol-3-yl, 2-hydroxy-6-methylpyridin-3-yl, 2-methyl-1H-benzimidazol-5-yl, 2-methyl-3H-benzimidazol-5-yl, 2-methylpyridin-3-yl, 2-methyl-6-trifluoromethylpyridin-3-yl, 2-methylthiazol-5-yl, 2-(morpholin-4-yl)-pyridin-4-yl, 2-(morpholin-4-yl)-pyrimidin-5-yl, 2-(pyrrolidin-1-yl)-pyridin-4-yl, 3,5-dimethyl-1H-pyrazol-4-yl, 3-amino-5,6-dimethylpyrazin-2-yl, 3-amino-5-methylpyrazin-2-yl, 3-aminopyrazin-2-yl, 3-dimethylamino-4-methylphenyl, 3-dimethylaminophenyl, 3H-benzimidazol-5-yl, 1H-benzimidazol-5-yl, 3-methylsulfonylamino-2-methylphenyl, 3-methylsulfonylaminophenyl, 3-methylisoxazol-4-yl, 3-(morpholin-4-yl)-phenyl, 3-(piperidin-1-yl)-phenyl, 3-(pyrrolidin-1-yl)-phenyl, 4-(2,2,2-trifluoroethoxy)phenyl, 4,6-dimethylpyridin-3-yl, 4-amino-2-ethylsulfanylpyrimidin-5-yl, 4-amino-2-methylpyrimidin-5-yl, 4-chloro-3-methylsulfonylaminophenyl, 4-chloro-3-sulfamoylphenyl, 4-methyl-3-methylaminophenyl, 4-methylthiazol-5-yl, pyridin-2-yl, 5,6,7,8-tetrahydroquinolin-3-yl, 5-amino-1-phenyl-1H-pyrazol-4-yl, 5-methylsulfonyl-2-methylphenyl, 5-methyl-1-phenyl-1H-pyrazol-4-yl, 5-methylisoxazol-3-yl, 5-methylpyridin-3-yl, 5-methylpyrazin-2-yl, 6-chloropyridin-3-yl, 6-cyanopyridin-3-yl, 6-dimethylaminopyridin-3-yl, 6-ethynylpyridin-3-yl, 6-methoxymethylpyridin-3-yl, 6-methoxypyridin-3-yl, 6-methyl-2-methylaminopyridin-3-yl, 6-methylaminopyrazin-2-yl, 6-methylpyridin-3-yl, 6-(morpholin-4-yl)-pyridin-3-yl, 6-(pyrrolidin-1-yl)-pyridin-3-yl, imidazo[1,2-a]pyridin-2-yl, 6-trifluoromethylpyridin-3-yl, pyrimidin-4-yl, 4-methylsulfanylphenyl, 4-ethylsulfanylphenyl, 3-methoxycarbonylphenyl, 4-methoxycarbonylphenyl, 3-ethoxycarbonylphenyl, 4-ethoxycarbonylphenyl, 2-bromo-4-chlorophenyl, 2,3-dichlorophenyl, 3-chloro-4-(isopropylsulfonyl)thiophen-2-yl, 4-bromo-2-chlorophenyl, 4-methoxyphenyl, 4-ethoxyphenyl, 3-methoxyphenyl, 3-ethoxyphenyl, 2-methyl-thiophen-3-yl, 3-chloro-4-methyl-thiophen-2-yl, 5-bromo-thiophen-2-yl, 5-chloro-thiophen-2-yl, 5-methyl-thiophen-2-yl, 4-methyl-thiophen-2-yl, 3-methyl-thiophen-2-yl, 5-acetyl-thiophen-2-yl, pyridin-3-yl, pyridin-4-yl, 4-trifluoromethylphenyl, 4-ethylaminophenyl, 4-methylaminophenyl, 2-aminophenyl, 4-bromo-2-fluorophenyl, 2-chlorophenyl, 3-chloro-4-methylphenyl, 4-chloro-3-methylphenyl, 2-chloro-3-methylphenyl, 2-methylphenyl, 2-acetoxy-4-methylphenyl, 2-acetoxy-4-ethoxyphenyl, 2-acetoxy-4-methoxyphenyl, 4-trifluoromethylsulfanylphenyl, naphthalen-2-yl, 1,1-dimethylindan-4-yl, 3-isobutyrylaminophenyl, 3-(2,2-dimethylpropionylamino)phenyl, 2-bromophenyl, 2-fluorophenyl, 3-bromo-5-methylthiophen-2-yl, 3-chloro-6-fluorobenzo[b]thiophen-2-yl and 3,4-dichlorobenzo[b]thiophen-2-yl.

Heteroaryl is preferably a residue of a 5-membered to 10-membered, aromatic, monocyclic or bicyclic heterocycle containing 1, 2 or 3 heteroatoms selected from the group consisting of N, O and S, more preferably of a monocyclic 5-membered or 6-membered heterocycle containing 1, 2 or 3 heteroatoms selected from the group consisting of N, O and S. Even more preferably heteroaryl is selected from the group consisting of furyl, pyrrolyl, thienyl, thiazolyl, isothiazolyl, oxazolyl, isoxazolyl, pyrazolyl, imidazolyl, pyridazinyl, pyrazinyl, pyridinyl, pyrimidinyl, benzimidazolyl, benzothiazolyl, benzoxazolyl, quinolinyl, isoquinolinyl, quinoxalinyl, quinazolinyl, indolyl, benzofuranyl, benzodioxolyl, benzothiophenyl and indazolyl, in particular from the group consisting of furyl, pyrrolyl, thienyl, thiazolyl, oxazolyl, pyrazolyl, imidazolyl, pyrazinyl, pyridinyl and pyrimidinyl.

Aryl is preferably phenyl.

m is preferably 0 or 2.

n is preferably 1 or 3, more preferably 1. I.e., in preferred embodiments of the invention the compounds of formula I are acylated arylcycloalkylamines of the formula Ia, i.e. acylated 2-arylcyclopropylamines, or of the formula Ib, i.e. acylated 2-arylcyclopentylamines. In the compounds of the formulae Ia and Ib the residues $R^1$ and $R^2$ can have any of the general or preferred or specific meanings indicated above or below. In the compounds of the formula Ia the groups $R^1$ and $R^2$—CO—NH— are preferably present in trans position with respect to each other.

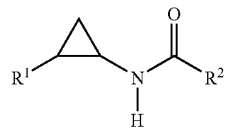

Ia

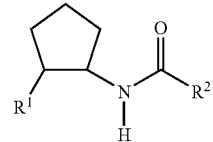

Ib

Preferred compounds of the formula I are those compounds in which one or some or all of the structural moieties and groups contained therein have preferred meanings, more preferred meanings, even more preferred meanings or most preferred meanings defined above, all combinations of such preferred meanings etc. and/or of specific meanings of a group being a subject of the present invention. With respect to all preferred compounds of the formula I the present invention also includes all stereoisomeric forms and mixtures thereof in all ratios, and their pharmaceutically acceptable salts.

A compound of the formula I or a salt thereof can be prepared, for example, by a process which comprises the acylation of an arylcycloalkylamine of the formula II with a carboxylic acid of the formula $R^2$—COOH or a derivative thereof, which process also is a subject of the present invention.

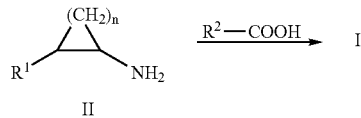

Suitable derivatives of the carboxylic acids of the formula $R^2$—COOH are, for example, carboxylic acid chlorides, esters including $C_1$–$C_4$-alkyl esters, such as methyl esters or ethyl esters, optionally substituted aryl esters, such as phenyl esters or nitrophenyl esters, or activated esters, or anhydrides or mixed anhydrides. In the compounds of the formula II and the carboxylic acids of the formula $R^2$—COOH and their derivatives the groups $R^1$ and $R^2$ and the number n have the meanings indicated above with respect to the compounds of the formula I, or else functional groups can be present in protected form or in the form of a precursor. For example, when a compound of the formula I is to be prepared which contains a carboxylic acid group or an amino group, it may be appropriate that in the acylation reaction these groups are present in protected form, for example as an ester such as a tert-butyl ester or benzyl ester instead of the free carboxylic acid group, or as an acylated amino group such as a tert-butoxycarbonylamino group or benzyloxycarbonylamino group instead of the free amino group, and only subsequent to the acylation the desired final groups are liberated by deprotection. Suitable protective group strategies which may be used in the synthesis of the compounds of formula I are known to the person skilled in the art. An example of a precursor group of a functional group is the nitro group which can be converted into an amino group by reduction, for example by catalytic hydrogenation, after the acylation reaction.

The acylation reactions can be carried out under standard conditions known to the person skilled in the art. In many cases the reaction is favorably performed in an inert solvent or diluent, for example a hydrocarbon or a chlorinated hydrocarbon, such as toluene, 1,2-dichloroethane or methylene chloride, an ether, such as tetrahydrofuran, dioxane or 1,2-dimethoxyethane, an alcohol such as methanol, ethanol or isopropanol, an amide such as N,N-dimethylformamide or N-methylpyrrolidone, acetonitrile, water, or a else a mixture of two or more solvents or diluents. Depending on the individual case, it may be advantageous to perform the reaction in the presence of a base, for example an inorganic base such as sodium hydroxide, sodium carbonate or sodium hydrogen carbonate, or an organic base such as triethylamine, ethyldiisopropylamine, N-ethylmorpholine or pyridine, and/or in the presence of an acylation catalyst such as 4-dimethylaminopyridine.

If a carboxylic acid of the formula $R^2$—COOH is to be used in the acylation of a compound of the formula II, it is often advantageous to activate the acid or a salt thereof with a condensation agent or coupling agent, for example an agent like those commonly used in peptide chemistry for the formation of amide bonds. Examples of suitable coupling agents are carbodiimides such as dicyclohexylcarbodiimide or diisopropylcarbodiimide, TOTU, i.e. O-((cyano(ethoxycarbonyl)methylene)amino)-N,N,N',N'-tetramethyluronium tetrafluoroborate, HATU, i. e. O-(7-azabenzotriazol-1-yl)-1, 1,3,3-tetramethyluronium hexafluorophosphate, chloroformic acid esters like ethyl chloroformate or isobutyl chloroformate, tosyl chloride, propylphosphonic acid anhydride or carbonyldiimidazole. Depending on the individual case, the suitable reaction temperature may lie within a wide range. For example, when employing into the acylation reaction a carboxylic acid in the presence of a coupling agent or a carboxylic acid chloride, the reaction can often be carried out at room temperature.

Subsequent to the acylation reaction, besides the abovementioned deprotection of protected groups or the conversion of a precursor group into the desired final group, optionally further functionalizations or modifications of the obtained compounds can be carried out and suitable functional groups can, for example, be esterified, amidated, transesterified, hydrolyzed, alkylated, sulfonylated, acylated, reduced, oxidized, converted into a salt, or subjected to other reactions.

The starting compounds for the preparation of the compounds of the formula I are commercially available or can be prepared according to or analogously to literature procedures, for example as described in Aggarwal et al., Organic Letters 3 (2001) 2785; Wiehl et al., Chem. Ber. 119 (1986) 2668; Brown et al., Tetrahedron 43 (1987) 4071; U.S. Pat. No. 6,008,240; or Coutts et al., Cell. Mol. Neurobiol. 7 (1987) 271) (the content of each of which is incorporated herein by reference).

All reactions for the synthesis of the compounds of the formula I are per se well-known to the skilled person and can be carried out under standard conditions according to or analogously to procedures described in the literature, for example in Houben-Weyl, Methoden der Organischen Chemie (Methods of Organic Chemistry), Thieme-Verlag, Stuttgart, or Organic Reactions, John Wiley & Sons, New York, the content of each of which is incorporated herein by reference. As mentioned above, depending on the circumstances of the individual case, in order to avoid side reactions during the synthesis of a compound of the formula I, in any reaction step it can be necessary or advantageous to temporarily block functional groups by introducing protective groups and to deprotect them in a later stage of the synthesis, or introduce functional groups in the form of precursor groups which in a later reaction step are converted into the desired functional groups. Such synthesis strategies and protective groups and precursor groups which are suitable in an individual case are known to the skilled person. If desired, the compounds of the formula I can be purified by customary purification procedures, for example by recrystallization or chromatography.

DETAILED DESCRIPTION OF THE INVENTION

Definition of Terms

As used above, and throughout the description of the invention, the following terms, unless otherwise indicated, shall be understood to have the following meanings.

"Patient" includes both human and other mammals.

"Pharmaceutically effective amount" is meant to describe an amount of a compound, composition, medicament or other active ingredient effective in producing the desired therapeutic effect.

"Optionally substituted" means either unsubstituted or substituted one or more times by substituents, which may be the same, or different.

"Partially unsaturated" is meant that there is at least one unsaturated bond that occurs in the group.

EMBODIMENTS

The compounds of the formula I are useful pharmaceutically active compounds which upregulate the expression of endothelial NO synthase and can be employed as medicaments for the treatment of various diseases. In the context of the present invention, treatment is understood as comprising both therapy, including alleviation and cure, of disease symptoms and prevention or prophylaxis of disease symptoms, such as, for example, the prevention of the appearance of asthmatic disease symptoms or the prevention of myocardial infarction or of myocardial reinfarction in relevant patients. The diseases or disease symptoms can be acute or chronic. Diseases which can be treated with the compounds of the formula I include, for example, cardiovascular diseases like stable and unstable angina pectoris, coronary heart disease, Prinzmetal angina (spasm), acute coronary syndrome, heart failure, myocardial infarction, stroke, thrombosis, peripheral artery occlusive disease (PAOD), endothelial dysfunction, atherosclerosis, restenosis, endothel damage after PTCA, hypertension including essential hypertension, pulmonary hypertension and secondary hypertension (renovascular hypertension, chronic glomerulonephritis), erectile dysfunction and ventricular arrhythmia. Further, the compounds of the formula I lower the cardiovascular risk of postmenopausal women and of women taking contraceptives. Compounds of the formula I can additionally be used in the treatment, i. e. the therapy and prevention, of diabetes and diabetes complications (nephropathy, retinopathy), angiogenesis, asthma bronchiale, chronic renal failure, cirrhosis of the liver, osteoporosis, restricted memory performance or a restricted ability to learn. Preferred indications are stable angina pectoris, coronary heart disease, hypertension, endothelial dysfunction, atherosclerosis and diabetes complications.

The compounds of the formula I can be used in combination with other pharmaceutically active compounds, preferably with compounds which are able to enhance the effect of the compounds of the formula I. Examples of such other compounds include statins; ACE inhibitors; AT1 antagonists; argininase inhibitors; PDE V inhibitors; calcium antagonists; alpha blockers; beta blockers; thiamazole (methimazole) and analogous compounds; arginine; tetrahydrobiopterin; vitamins, in particular vitamin C and vitamin B6; niacine.

The compounds of the formula I and their pharmaceutically acceptable salts, optionally in combination with other pharmaceutically active compounds, can be administered to animals, preferably to mammals, and in particular to humans, as pharmaceuticals by themselves, in mixtures with one another or in the form of pharmaceutical preparations. Further subjects of the present invention therefore also are the compounds of the formula I and their pharmaceutically acceptable salts for use as pharmaceuticals, their use as transcription stimulating agents or upregulating agents of endothelial NO synthase, for example in conditions in which an increased expression of said enzyme or an increased NO level or the normalization of a decreased NO level in a patient is desired, and in particular their use in the treatment, i. e. the therapy and prevention, of the above-mentioned syndromes, as well as their use for preparing medicaments for these purposes. Furthermore, a subject of the present invention are pharmaceutical preparations (or pharmaceutical compositions) which comprise an effective dose of at least one compound of the formula I and/or a pharmaceutically acceptable salt thereof and a pharmaceutically acceptable carrier, i.e. one or more pharmaceutically acceptable carrier substances or vehicles and/or additives or excipients.

All discussions herein regarding the compounds of formula I and their pharmaceutically acceptable salts which are the subject of the invention as compounds per se, for example, processes for preparing them and details regarding their use as pharmaceuticals, are meant to apply to compounds of the invention excluded by the provisos.

A subject of the present invention also are those compounds of the formula I which have already been known per se and are excluded by the provisos from the above-defined compounds of the formula I which are claimed as compounds per se, and their pharmaceutically acceptable salts, for use as transcription stimulating agent or upregulating agent of endothelial NO synthase, for use as pharmaceuticals and for use in the treatment of the diseases mentioned above, and pharmaceutical preparations which comprise an effective dose of at least one of these excluded compounds and/or a pharmaceutically acceptable salt thereof and a pharmaceutically acceptable carrier. All statements above and below relating, for example, to the compounds of the formula I for use as pharmaceutical, explicitly apply also to these excluded compounds. Thus, for example, a subject of the present invention are acylated arylcycloalkylamines of the formula I,

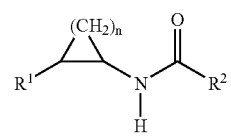

in any of their stereoisomeric forms and mixtures thereof in any ratio, and the pharmaceutically acceptable salts thereof, wherein in the formula I:

$R^1$ is aryl or heteroaryl both of which are unsubstituted or substituted by one or more identical or different substituents selected from the group consisting of $C_1$–$C_6$-alkyl, halogen, $CF_3$, $C_1$–$C_6$-alkoxy, $C_1$–$C_6$-alkylmercapto, —CN, $COOR^{10}$, $CONR^{11}R^{12}$, $NR^{13}R^{14}$, $S(O)_mR^{15}$ and $S(O)_2NR^{16}R^{17}$;

$R^2$ is aryl or heteroaryl both of which are unsubstituted or carry one or more identical or different substituents selected from the group consisting of:

halogens; —CN; $NH_2$; unsubstituted and at least monosubstituted $C_1$–$C_{10}$-alkyl, $C_2$–$C_{10}$-alkenyl, $C_2$–$C_{10}$-alkynyl, $C_1$–$C_{10}$-alkoxy, $C_1$–$C_{10}$-alkylamino and di($C_1$–$C_{10}$-alkyl)amino, the substituents of which are selected from the group consisting of F, OH, $C_1$–$C_8$-alkoxy, aryloxy, $C_1$–$C_8$-alkylmercapto, $NH_2$, $C_1$–$C_8$-alkylamino and di($C_1$–$C_8$-alkyl)amino; $C_3$–$C_5$-alkandiyl; phenyl; heteroaryl; aryl-substituted or heteroaryl-substituted $C_1$–$C_4$-alkyl; $CF_3$; $NO_2$; OH; phenoxy; benzyloxy; ($C_1$–$C_{10}$-alkyl)-COO—; $S(O)_mR^{20}$; SH; phenylamino; benzylamino; ($C_1$–$C_{10}$-alkyl)-CONH—; ($C_1$–$C_{10}$-alkyl)-CO—N($C_1$–$C_4$-alkyl)-; phenyl-CONH—; phenyl-CO—N($C_1$–$C_4$-alkyl)-; heteroaryl-CONH—; heteroaryl-CO—N($C_1$–$C_4$-alkyl)-; ($C_1$–$C_{10}$-alkyl)-CO—; phenyl-CO—; heteroaryl-CO—; $CF_3$—CO—; —$OCH_2O$—; —$OCF_2O$—; —$OCH_2CH_2O$—; —$CH_2CH_2O$—; $COOR^{21}$; $CONR^{22}R^{23}$; $C(NH)$—$NH_2$; $SO_2NR^{24}R^{25}$; $R^{26}SO_2NH$—; $R^{27}SO_2N(C_1$–$C_6$-alkyl)-; and a residue of a saturated or at least monounsaturated aliphatic, monocyclic 5-membered to 7-membered heterocycle containing 1, 2 or 3 heteroatoms selected from the group consisting of N, O and S, which heterocycle can be substituted by one or more substituents selected from the group consisting of halogens, $C_1$–$C_3$-alkyl, $C_1$–$C_3$-alkoxy, OH, oxo and $CF_3$, where said heterocycle can optionally be condensed to the said aryl group or heteroaryl group representing $R^2$; wherein all aryl, heteroaryl, phenyl, aryl-containing, heteroaryl-containing and phenyl-containing groups, which are optionally present in the said substituents of the said aryl group or heteroaryl group representing $R^2$, can be substituted by one or more substituents selected from the group consisting of halogens, —CN, $C_1$–$C_3$-alkyl, OH, $C_1$–$C_3$-alkoxy and $CF_3$;

$R^{10}$ is H, $C_1$–$C_6$-alkyl or benzyl wherein the phenyl group can be substituted by one or more identical or different substituents from the group consisting of halogens, —CN, $C_1$–$C_3$-alkyl, $C_1$–$C_3$-alkoxy and $CF_3$;

$R^{11}$ is selected from the group consisting of:

H; $C_1$–$C_6$-alkyl which can be substituted by phenyl; phenyl; indanyl; and heteroaryl; wherein each of the aromatic groups is unsubstituted or carries one or more identical or different substituents from the group consisting of halogens, —CN, $C_1$–$C_3$-alkyl, $C_1$–$C_3$-alkoxy and $CF_3$;

$R^{12}$ is H or $C_1$–$C_6$-alkyl;

$R^{13}$ is selected from the group consisting of:
H; $C_1$–$C_6$-alkyl; and unsubstituted and substituted phenyl, benzyl, heteroaryl, phenyl-CO—, and heteroaryl-CO—, the substituents of which are selected from the group consisting of halogens, —CN, $C_1$–$C_3$-alkyl, $C_1$–$C_3$-alkoxy and $CF_3$, wherein one or more of these substituents can be present;

$R^{14}$ is H or $C_1$–$C_6$-alkyl;

$R^{15}$ is selected from the group consisting of:
$C_1$–$C_6$-alkyl; $CF_3$; and substituted and unsubstituted phenyl and heteroaryl, the substituents of which are selected from the group consisting of halogens, —CN, $C_1$–$C_3$-alkyl, $C_1$–$C_3$-alkoxy and $CF_3$, wherein one or more of these substituents can be present;

$R^{16}$, independently from $R^{11}$, is defined as $R^{11}$;

$R^{17}$, independently from $R^{12}$, is defined as $R^{12}$;

$R^{20}$ is selected from the group consisting of:
$C_1$–$C_{10}$-alkyl which can be substituted by one or more substituents selected from the group consisting of F, OH, $C_1$–$C_8$-alkoxy, aryloxy, $C_1$–$C_8$-alkylmercapto, $C_1$–$C_8$-alkylamino and di($C_1$–$C_8$-alkyl)amino; $CF_3$; and substituted and unsubstituted phenyl and heteroaryl, the substituents of which are selected from the group consisting of halogens, —CN, $C_1$–$C_3$-alkyl, $C_1$–$C_3$-alkoxy and $CF_3$, wherein one or more of these substitutents can be present;

$R^{21}$ is selected from the group consisting of:
H; $C_1$–$C_{10}$-alkyl which can be substituted by one or more substituents selected from the group consisting of F, $C_1$–$C_8$-alkoxy and di($C_1$–$C_8$-alkyl)amino; aryl-($C_1$–$C_4$-alkyl)- and heteroaryl-($C_1$–$C_4$-alkyl)- which can be substituted by one or more substituents selected from the group consisting of halogens, $C_1$–$C_4$-alkoxy and di($C_1$–$C_6$-alkyl)amino;

$R^{22}$ is selected from the group consisting of:
H; $C_1$–$C_{10}$-alkyl which can be substituted by one or more substituents selected from the group consisting of F, $C_1$–$C_8$-alkoxy, di($C_1$–$C_8$-alkyl)amino and phenyl; phenyl; indanyl; and heteroaryl; wherein each of the aromatic groups can be unsubstituted or carry one or more substituents selected from the group consisting of halogens, —CN, $C_1$–$C_3$-alkyl, $C_1$–$C_3$-alkoxy and $CF_3$;

$R^{23}$ is H or $C_1$–$C_{10}$-alkyl;

$R^{24}$, independently from $R^{22}$, is defined as $R^{22}$;

$R^{25}$, independently from $R^{23}$, is defined as $R^{23}$;

$R^{26}$, independently from $R^{20}$, is defined as $R^{20}$;

$R^{27}$, independently from $R^{20}$, is defined as $R^{20}$;

heteroaryl is a residue of a 5-membered to 10-membered, aromatic, monocyclic or bicyclic heterocycle containing one or more heteroatoms selected from the group consisting of N, O and S;

aryl is phenyl, naphth-1-yl or naphth-2-yl;

m is 0, or 2;

n is 1, 2, 3 or 4;

for use as pharmaceutical.

With respect to compounds of the formula I for use as pharmaceutical, all explanations given above with respect to the compounds of the formula I per se likewise apply. Thus, a further subject of the invention also are compounds of the formula I for use as pharmaceutical, in which one or more, including all, of the groups and numbers in the definition of the compounds have preferred meanings, more preferred meanings, even more preferred meanings or most preferred meanings or any specific meaning.

The pharmaceuticals according to the invention can be administered orally, for example in the form of pills, tablets, lacquered tablets, sugar-coated tablets, granules, hard and soft gelatin capsules, aqueous, alcoholic or oily solutions, syrups, emulsions or suspensions, or rectally, for example in the form of suppositories. Administration can also be carried out parenterally, for example subcutaneously, intramuscularly or intravenously, in the form of solutions for injection or infusion. Other suitable administration forms are, for example, percutaneous or topical administration, for example in the form of ointments, tinctures, sprays or transdermal therapeutic systems, or the inhalative administration in the form of nasal sprays or aerosol mixtures, or, for example, microcapsules, implants or rods. The preferred administration form depends, among others, on the disease to be treated and on its severity.

The amount of a compound of the formula I and/or its pharmaceutically acceptable salts in the pharmaceutical preparations normally ranges from about 0.2 to about 800 mg, preferably from about 0.5 to about 500 mg, in particular from about 1 to about 200 mg, per dose, but depending on the type of the pharmaceutical preparation it may also be higher. The pharmaceutical preparations usually comprise from about 0.5 to about 90% by weight of the compounds of the formula I and/or their pharmaceutically acceptable salts. The production of the pharmaceutical preparations can be carried out in a manner known per se. To this end, one or more compounds of the formula I and/or their pharmaceutically acceptable salts, together with one or more solid or liquid pharmaceutical carrier substances and/or additives (or auxiliary substances) and, if desired, in combination with other pharmaceutically active compounds having therapeutic or prophylactic action, are brought into a suitable administration form or dosage form which can then be used as a pharmaceutical in human or veterinary medicine.

For the production of pills, tablets, sugar-coated tablets and hard gelatin capsules it is possible to use, for example, lactose, starch, for example maize starch, or starch derivatives, talc, stearic acid or its salts, etc. Soft gelatin capsules and suppositories can comprise, for example, fats, waxes, semisolid and liquid polyols, natural or hardened oils, etc. Suitable carrier substances for the preparation of solutions, for example of solutions for injection, or of emulsions or syrups are, for example, water, physiologically sodium chloride solution, alcohols such as ethanol, glycerol, polyols, sucrose, invert sugar, glucose, mannitol, vegetable oils, etc. It is also possible to lyophilize the compounds of the formula I and their pharmaceutically acceptable salts and to use the resulting lyophilisates, for example, for preparing preparations for injection or infusion. Suitable carriers for microcapsules, implants or rods are, for example, copolymers of glycolic acid and lactic acid.

Besides the compound or compounds of the invention and carrier substances, the pharmaceutical preparations can also contain additives such as, for example, fillers, disintegrants, binders, lubricants, wetting agents, stabilizers, emulsifiers, dispersants, preservatives, sweeteners, colorants, flavorings, aromatizers, thickeners, diluents, buffer substances, solvents, solubilizers, agents for achieving a depot effect, salts for altering the osmotic pressure, coating agents or antioxidants.

The dosage of the compound of the formula I to be administered and/or of a pharmaceutically acceptable salt thereof depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the use is for the therapy of a acute or chronic disease or prophylactic, or on whether other active compounds are administered in addition to compounds of the formula I. In general, a daily dose of from about 0.01 to about 100 mg/kg, preferably from about 0.1 to about 10 mg/kg, in particular from about 0.3 to about 5 mg/kg (in each case mg per kg of bodyweight) is appropriate for administration to an adult weighing approximately 75 kg in order to obtain the desired results. The daily dose can be administered in a single dose or, in particular when larger amounts are administered, be divided into several, for example two, three or four individual doses. In some cases, depending on the individual response, it may be necessary to deviate upwards or downwards from the given daily dose.

The compounds of the formula I can also be used for other purposes than those indicated in the foregoing. Non-limiting examples include diagnostic purposes, such as the use in the examination of cell or tissue samples, the use as biochemical tools and the use as intermediates for the preparation of further compounds, e.g. pharmaceutically active compounds.

EXAMPLES

General Synthetic Procedure for Acylations of Arylcyclopropylamines 304 mg (0.928 mmol, 1.05 equivalents) of TOTU and 323 µl (1.857 mmol, 2.1 equivalents) of ethyldiisopropylamine were added to 0.973 mmol (1.0 equivalent) of the respective carboxylic acid in 2 ml of absolute dimethylformamide at 0° C. and the mixture was stirred for 20 minutes at 0° C. Subsequently, 0.884 mmol (1.0 equivalent) of the respective arylcycloalkylamine hydrochloride, dissolved in 2 ml of absolute dimethylformamide, were added and the mixture was stirred for 30 minutes at 0° C. and for 24 h at room temperature. The reaction mixture was filtered, the filter cake washed with 20 ml of ethyl acetate and the resulting solution washed with 20 ml of 5% aqueous sodium hydrogencarbonate solution and 20 ml of 5% aqueous sodium chloride solution. The organic phase was dried over Chromabond XTR and evaporated. The obtained raw product was purified by preparative HPLC (RP-18, acetonitrile/water +0.1% trifluoroacetic acid).

According to the aforesaid procedure, starting from racemic trans-2-phenylcyclopropylamine and the respective carboxylic acid of the formula $R^2$—COOH, the N-(trans-2-phenylcyclopropyl)carboxamides of the formula Ic

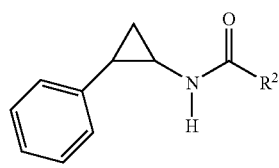

Ic listed in Table 1 were prepared. In Table 1, besides the denotations of the residue $R^2$, the mass numbers of the (M+H)$^+$ peak in the mass spectra (MS) obtained from the prepared compounds, and the HPLC retention times RT (in minutes) are given.

HPLC method A

Column: YMC J'Sphere ODS H80, 33×2 mm, 4µ; temperature: 30° C.; flow: 1.000 ml/min; eluent A: acetonitrile+ 0.05% HCOOH; eluent B: water+0.05% HCOOH; gradient: time 0.00 min: 10% eluent A+90% eluent B, time 2.50 min: 95% eluent A+5% eluent B, time 3.30 min: 95% eluent A+5% eluent B, time 3.35 min: 10% eluent A+90% eluent B.

HPLC method B

Column: Merck Purospher Star, 55×2 mm, 3µ; temperature: room temperature; flow: 0.45 ml/min; eluent A: acetonitrile+0.1% HCOOH; eluent B: water+0.1% HCOOH; gradient: time 0.00 min: 5% eluent A+95% eluent B, time 5.00 min: 95% eluent A+5% eluent B, time 7.00 min: 95% eluent A+5% eluent B, time 8.00 min: 5% eluent A+95% eluent B.

HPLC method C

Column: YMC J'Sphere ODS H80, 33×2 mm, 3µ; room temperature; flow: 1.000 ml/min; eluent A: acetonitrile; eluent B: water+0.05% trifluoroacetic acid; gradient: time 0.00 min: 10% eluent A+90% eluent B, time 2.50 min: 95% eluent A+5% eluent B, time 3.30 min: 95% eluent A+5% eluent B.

TABLE 1

Example compounds of formula Ic

| Ex. No. | $R^2$ | MS (M + H)$^+$ | HPLC RT (min) | HPLC Method |
|---|---|---|---|---|
| 1 | 2,4-dimethyloxazol-5-yl | 257 | 1.999 | A |
| 2 | 3-amino-5-methylpyrazin-2-yl (a) | 267 | 4.55 | B |
| 3 | 2-cyclopropyl-4-methylthiazol-5-yl | 299 | 4.51 | B |
| 4 | 2,6-dimethylpyridin-3-yl | 266 | 1.119 | B |
| 5 | 3-amino-5,6-dimethylpyrazin-2-yl (a) | 283 | 4.73 | B |
| 6 | 6-methylaminopyrazin-2-yl | 269 | 2.057 | A |
| 7 | 3-methylsulfonylamino-4-methylphenyl | 345 | 4.18 | B |
| 8 | 3-methylsulfonylaminophenyl | 331 | 2.057 | A |
| 9 | 6-(morpholin-4-yl)pyridin-3-yl | 323 | 1.902 | A |
| 10 | 5,6,7,8-tetrahydroquinolin-3-yl (a) | 293 | 3.30 | B |
| 11 | 6-methoxypyridin-3-yl (a) | 269 | 4.22 | B |
| 12 | 2-methylthiazol-5-yl | 259 | 4.02 | B |
| 13 | 3-(pyrrolidin-1-yl)phenyl (a) | 307 | 5.04 | B |
| 14 | 3-(piperidin-1-yl)phenyl (a) | 321 | 3.63 | B |
| 15 | 3-(4-methylpiperazin-1-yl)phenyl | 336 | 1.437 | A |
| 16 | 3-(morpholin-4-yl)phenyl (a) | 323 | 4.36 | B |
| 17 | 2,5-dimethyl-1-(thiophen-2-ylmethyl)-1H-pyrrol-3-yl | 351 | 5.04 | B |
| 18 | 2-methyl-3H-benzimidazol-5-yl | 292 | 1.300 | A |
| 19 | 3-chloro-4-isopropylsulfonyl-thiophen-2-yl | 384 | 2.396 | A |
| 20 | 5-methyl-1-phenyl-1H-pyrazol-4-yl | 318 | 2.324 | A |
| 21 | 1-phenyl-5-trifluoromethyl-1H-pyrazol-4-yl | 372 | 2.508 | A |
| 22 | 2,5-dimethyl-1-(pyridin-4-ylmethyl)-1H-pyrrol-3-yl | 346 | 2.679 | A |
| 23 | 2,4-dimethylthiazol-5-yl | 273 | 2.050 | A |
| 24 | 2-aminopyridin-3-yl | 254 | 1.137 | A |
| 25 | 6-methylpyridin-3-yl | 253 | 1.611 | A |
| 26 | 2-chloro-6-methylpyridin-3-yl | 287 | 2.084 | A |
| 27 | 6-methoxymethylpyridin-3-yl (a) | 283 | 3.80 | B |
| 28 | 3-aminopyrazin-2-yl | 255 | 2.168 | A |
| 29 | 1H-indol-6-yl | 277 | 4.44 | B |
| 30 | 1H-indol-5-yl | 277 | 4.35 | B |
| 31 | 1H-indol-4-yl | 277 | 4.35 | B |
| 32 | 3-dimethylaminophenyl | 281 | 2.149 | A |
| 33 | 2-amino-4,6-dimethylpyridin-3-yl (a) | 282 | 2.84 | B |
| 34 | 2,3-dichlorophenyl | 306 | 4.88 | B |
| 35 | 2,4-dimethylphenol | 266 | 4.84 | B |
| 36 | 2,4-difluorophenyl | 274 | 2.73 | B |

TABLE 1-continued

Example compounds of formula Ic

| Ex. No. | R² | MS (M + H)⁺ | HPLC RT (min) | HPLC Method |
|---|---|---|---|---|
| 37 | 5-methylthiophen-2-yl | 258 | 4.68 | B |
| 38 | 5-chlorothiophen-2-yl | 278 | 4.95 | B |
| 39 | 4-fluorophenyl | 256 | 2.32 | C |

(a) The compound was obtained as salt with trifluoroacetic acid.

Example 40

4-Fluoro-N-(trans-2-phenylcyclopropyl)benzamide (Enantiomer 1)

Racemic 4-fluoro-N-(trans-2-phenylcyclopropyl)benzamide (compound of Example 39) was separated into the enantiomers by preparative HPLC on a chiral phase (Chiralpak AD; eluent: acetonitrile/isopropanol (120/5)+0.1% diethylamine).

MS: m/e=256 (M+H)⁺. HPLC: RT=4.07 min (column: Daicel Chiralpak AD, 250×4.6 mm, 10μ; eluent: acetonitrile/isopropanol (120/5)+0.1% diethylamine; flow rate: 1.000 ml/min).

Example 41

4-Fluoro-N-(trans-2-phenylcyclopropyl)benzamide (Enantiomer 2)

The title compound was prepared as described in Example 40 by separation of racemic 4-fluoro-N-(trans-2-phenylcyclopropyl)benzamide.

MS: m/e=256 (M+H)⁺. HPLC: RT=4.47 min (column: Daicel Chiralpak AD, 250×4.6 mm, 10μ; eluent: acetonitrile/isopropanol (120/5)+0.1% diethylamine; flow rate: 1.000 ml/min).

Experimental

Determination of Activation of eNOS Transcription

Activation of eNOS transcription was determined as described in detail in Li et al., "Activation of protein kinase C alpha and/or epsilon enhances transcription of the human endothelial nitric oxide synthase gene", Mol. Pharmacol. 53 (1998) 630, the content of which is incorporated herein by reference.

Briefly, a 3.5 kB long fragment 5' of the starting codon of the eNOS gene was cloned, sequenced and cloned in firefly luciferase expression plasmids to monitor activation of the eNOS promoter by reporter gene activity. A human endothelial cell line stable transfected and expressing this promoter-reporter construct was used for compound testing. Cells were incubated for 18 h with compounds.

All compounds were dissolved in sterile dimethyl sulfoxide (DMSO). A final concentration of 0.5% DMSO in complete medium was allowed. Induction of reporter gene expression in these cells was measured using a standard luciferase assay system (Promega, Cat. No E150) according to the manufacturer's instructions. Luciferase induction in cells incubated with compounds were compared to those incubated with solvent alone. The ratio of both activities (transcription induction ratio, TIR) was plotted as a function of compound concentration. Typically, TIR values started at low concentrations at a ratio of 1, indicating no compound effect, and extended up to a maximum TIR value TIR(max) which indicates the increase of the eNOS transcription. $EC_{50}$ values of transcription induction ratios as a function of compound concentration were determined graphically.

The effect of compounds on eNOS-transcription was confirmed in a second assay based on eNOS protein detection. Primary human umbilical vein cord endothelial cells (HUVEC) were isolated and cultivated according to standard procedures. Confluent cells were incubated with compounds for 18 h and the effect on eNOS protein expression determined by a quantitative Western blotting procedure. After compounds incubation, HUVEC were lysed in ice-cold lysis buffer containing 10 mM Tris-HCl, pH 8.0, 1% SDS and protease inhibitors. The lysate was subjected to a standard denaturating polyacrylamide gel electrophoresis and blotted to nitrocellulose membranes. Using a specific primary monoclonal antibody (Transduction Laboratories, UK) and alkaline phosphatase labelled secondary antibody (Jackson Labs), a specific eNOS protein band was visualized and quantified based on a chemifluorescence detection method.

The results are shown in Table 2.

TABLE 2 eNOS transcription induction ratios

| Compound of example no. | $EC_{50}$ (μM) |
|---|---|
| 1 | 18 |
| 2 | 0.060 |
| 3 | 0.30 |
| 4 | 0.33 |
| 5 | 0.16 |
| 6 | 0.32 |
| 7 | 1.8 |
| 8 | 2.0 |
| 9 | 3.5 |
| 10 | 5.1 |
| 11 | 0.78 |
| 12 | 10 |
| 13 | 1.3 |
| 14 | 11 |
| 15 | 59 |
| 16 | 32 |
| 17 | <0.01 |
| 18 | 0.33 |
| 19 | 0.45 |
| 20 | 0.11 |
| 21 | 0.24 |
| 22 | 24 |
| 23 | 0.60 |
| 24 | 0.95 |
| 25 | 1.1 |
| 26 | 0.29 |
| 27 | 4.3 |
| 28 | 0.43 |
| 29 | 0.10 |
| 30 | 0.10 |
| 31 | 0.47 |
| 32 | 1.8 |
| 33 | 12 |
| 34 | 1.2 |
| 35 | 0.062 |
| 36 | 0.31 |
| 37 | 0.26 |
| 38 | 0.23 |
| 39 | 0.19 |
| 40 | 1.5 |
| 41 | 0.18 |

The effect of the compounds of the invention can also be investigated in the following animal models (animal experiments are preformed in accordance tot he German animal protection law and to the guidelines for the use of experimental animals as given by the Guide for the Care and Use of Laboratory Animals of the US National Institues of Health).

Animals and Treatment (Experiments A–C)

ApoE and eNOS deficient mice (C57BL/6J background, Jackson Laboratory, Bar Harbor, Me.) are used. All animals are 10 to 12 weeks of age and weigh 22 to 28 g. Three days before surgery mice are divided into 4 groups (apoE control, n=10 to 12; apoE with test compounds, n=10 to 12; eNOS control, n=10 to 12; eNOS with test compounds, n=10 to 12) and receive either a standard rodent chow (containing 4% fat and 0.001% cholesterol; in the following designated as placebo group) or a standard rodent chow+test compound (10 or 30 mg/kg/d p.o.).

A. Anti-hypertensive Effect in ApoE Knockout Mice

Blood-pressure is determined in conscious mice using a computerized tail-cuff system (Visitech Systems, Apex, N.C.). After treatment of ApoE deficient mice and eNOS deficient mice with the test compounds the blood pressure is compared to the results obtained with a placebo treatment.

B. Inhibition of Neointima Formation and Atherogenesis (Femoral Artery Cuff)

After 3 day treatment of ApoE deficient mice with the respective compound, (10 mg/kg/d pressed in chow), animals are anesthetized with an intraperitoneal injection of pentobarbital (60 mg/kg) followed by an intramuscular injection of xylazin (2 mg/kg) and a cuff is placed around the femoral artery as described in Moroi et al.(J. Clin. Invest. 101 (1998) 1225, the content of which is incorporated herein by reference). Briefly, the left femoral artery is dissected. A non-occlusive 2.0 mm polyethylene cuff made of PE-50 tubing (inner diameter 0.56 mm, outer diameter 0.965 mm, Becton Dickinson, Mountain View, Calif.) is placed around the artery and tied in place with two 7-0 sutures. The right femoral artery is isolated from the surrounding tissues but a cuff is not placed. Treatment with the respective compound is continued for 14 days after surgery. Then the animals are sacrificed. The aorta are taken for determination of vascular eNOS expressions by quantitative western blotting. Both femoral arteries are harvested, fixed in formalin and embedded in paraffin. 20 cross sections (10 µm) are cut from the cuffed portion of the left femoral artery and from the corresponding segment of the right artery. Sections are subjected to standard hematoxylin and eosin staining. Morphometric analyses are performed using an image analysis computer program (LeicaQWin, Leica Imaging Systems, Cambridge, GB). For each cross section the area of the lumen, the neointima and the media are determined. To this end, the neointima is defined as the area between the lumen and the internal elastic lamina and the media is defined as the area between the internal and the external elastic lamina. The ratio between the area of the neointima and the area of the media is expressed as the neointima/media ratio. The results obtained in the compound group are compared to those obtained in the placebo group.

C. Prevention of Atherosclerotic Plaque Formation in Chronic Treatment

ApoE deficient mice are treated for 16 weeks with the respective compound pressed in chow and finally sacrificed. Aortas are removed from each mouse, fixed in formalin and embedded in paraffin. Plaque formation is measured via lipid lesions formation in the aortas (from aortic arch to diaphragm) and is analyzed by oil red O staining. For quantifying the effect of the respective compound on vascular eNOS expression the femoral arteries are used in this experiment. The results obtained in the compound group are compared to those obtained in the placebo group.

D. Improvement of Coronary Function in Diseased ApoE Deficient Mice

Old Male wild-type C57BL/6J mice (Charles River Wiga GmbH, Sulzfeld), and apoE deficient mice (C57BL/6J background, Jackson Laboratory, Bar Harbor, Me.) 6 month of age and weighing 28 to 36 g are used in the experiments. Mice are divided into 3 groups (C57BL/6, n=8; apoE control, n=8; apoE with respective compound, n=8) and receive for 8 weeks either a standard rodent chow (containing 4% fat and 0.001% cholesterol) or a standard rodent chow+respective compound (30 mg/kg/d p.o.).

Mice are anesthetized with sodium pentobarbitone (100 mg/kg i.p.), and the hearts are rapidly excised and placed into ice-cold perfusion buffer. The aorta is cannulated and connected to a perfusion apparatus (Hugo Sachs Electronics, Freiburg, Germany) which is started immediately at a constant perfusion pressure of 60 mm Hg. Hearts are perfused in a retrograde fashion with modified Krebs bicarbonate buffer, equilibrated with 95% $O_2$ and 5% $CO_2$ and maintained at 37.5° C.

A beveled small tube (PE 50) is passed through a pulmonary vein into the left ventricle and pulled through the ventricular wall, anchored in the apex by a fluted end, and connected to a tip-micromanometer (Millar 1.4 French). The left atrium is cannulated through the same pulmonary vein and the heart switched to the working mode with a constant preload pressure of 10 mm Hg and an afterload pressure of 60 mm Hg. Aortic outflow and atrial inflow are continuously measured using ultrasonic flow probes (HSE/Transonic Systems Inc.). Coronary flow is calculated as the difference between atrial flow and aortic flow. All hemodynamic data are digitized at a sampling rate of 1000 Hz and recorded with a PC using spezialized software (HEM, Notocord).

Hearts are allowed to stabilize for 30 min. All functional hemodynamic data are measured during steady state, and during volume- and pressure loading.

Left ventricular function curves are constructed by varying pre-load pressure. For acquisition of preload curves, afterload is set at 60 mm Hg and preload is adjusted in 5 mm Hg steps over a range of 5 to 25 mm Hg. Hearts are allowed to stabilize at baseline conditions between pressure- and volume-loading.

We claim:

1. A compound of the formula I,

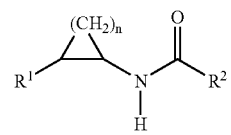

wherein:
R[1] is aryl, which is optionally substituted one or more times by $C_1$–$C_6$-alkyl, halogen, $CF_3$, $C_1$–$C_6$-alkoxy, $C_1$–$C_6$-alkylmercapto, —CN, COOR[10], CONR[11]R[12], NR[13]R[14], $S(O)_mR^{15}$ or $S(O)_2NR^{16}R^{17}$;

R[2] is oxazolyl, thiazolyl, or pyrrolyl, each of which is optionally substituted one or more times by:
halogen, —CN, —NH$_2$, $C_3$–$C_5$-alkandiyl, phenyl, heteroaryl, aryl-substituted $C_1$–$C_4$-alkyl, heteroaryl-substituted $C_1$–$C_4$-alkyl, —CF$_3$, —NO$_2$, —OH, phenoxy, benzyloxy, ($C_1$–$C_{10}$-alkyl)-COO—, —S(O)$_m$R$^{20}$, —SH, phenylamino, benzylamino, (C$_1$–C$_{10}$-alkyl)-CONH—, (C$_1$–C$_{10}$-alkyl)-CO—N(C$_1$–C$_4$-alkyl)-, phenyl-CONH—, phenyl-CO—N(C$_1$–C$_4$-alkyl)-, heteroaryl-CONH—, heteroaryl-CO—N(C$_1$–C$_4$-alkyl)-, (C$_1$–C$_{10}$-alkyl)-CO—, phenyl-CO—, heteroaryl-CO—, CF$_3$—CO—, —OCH$_2$O—, —OCF$_2$O—, —OCH$_2$CH$_2$O—, —CH$_2$CH$_2$O—, —COOR$^{21}$, —CONR$^{22}$R$^{23}$, —C(NH)—NH$_2$, —SO$_2$NR$^{24}$R$^{25}$, R$^{26}$SO$_2$NH—, R$^{27}$SO$_2$N(C$_1$–C$_6$-alkyl)-, optionally substituted C$_1$–C$_{10}$-alkyl, optionally substituted C$_2$–C$_{10}$-alkenyl, optionally substituted C$_2$–C$_{10}$-alkynyl, optionally substituted C$_1$–C$_{10}$-alkoxy, optionally substituted C$_1$–C$_{10}$-alkylamino, optionally substituted di(C$_1$–C$_{10}$-alkyl)amino, wherein the optional substituents of the optionally substituted substituents are selected from one or more of the group consisting of F, OH, C$_1$–C$_8$-alkoxy, aryloxy, C$_1$–C$_8$-alkylmercapto, NH$_2$, C$_1$–C$_8$-alkylamino and di(C$_1$–C$_8$-alkyl)amino, or a residue of a saturated or partially unsaturated aliphatic monocyclic 5- to 7-membered heterocycle containing 1, 2 or 3 heteroatoms selected from the group consisting of N, O and S, wherein the heterocycle is optionally substituted one or more times by halogen, C$_1$–C$_3$-alkyl, C$_1$–C$_3$-alkoxy, OH, oxo or CF$_3$, and wherein the heterocycle is optionally condensed to the aryl group or heteroaryl group representing R$^2$, and wherein for each oxazolyl, thiazolyl or pyrrolyl as R$^2$ bearing an aryl, heteroaryl, phenyl, aryl-containing, heteroaryl-containing or phenyl-containing group as an optional substituent, that each aryl, heteroaryl, phenyl, aryl-containing, heteroaryl-containing and phenyl-containing group is optionally substituted one or more times by halogen, —CN, C$_1$–C$_3$-alkyl, OH, C$_1$–C$_3$-alkoxy or CF$_3$;

R$^{10}$ is H, C$_1$–C$_6$-alkyl or benzyl, wherein the phenyl group of the benzyl is optionally substituted one or more times by halogen, —CN, C$_1$–C$_3$-alkyl, C$_1$–C$_3$-alkoxy or CF$_3$;

R$^{11}$ is H, C$_1$–C$_6$-alkyl, which is optionally substituted by phenyl, phenyl, indanyl or heteroaryl, wherein each phenyl, indanyl and heteroaryl is optionally substituted one or more times by halogen, —CN, C$_1$–C$_3$-alkyl, C$_1$–C$_3$-alkoxy or CF$_3$;

R$^{12}$ is H or C$_1$–C$_6$-alkyl;

R$^{13}$ is H, C$_1$–C$_6$-alkyl, optionally substituted phenyl, optionally substituted benzyl, optionally substituted heteroaryl, optionally substituted phenyl-CO—, or optionally substituted heteroaryl-CO—, wherein the optional substituents of the optionally substituted substituents are selected from one or more of the group consisting of halogen, —CN, C$_1$–C$_3$-alkyl, C$_1$–C$_3$-alkoxy and CF$_3$;

R$^{14}$ is H or C$_1$–C$_6$-alkyl;

R$^{15}$ is C$_1$–C$_6$-alkyl, CF$_3$, optionally substituted phenyl or optionally substituted heteroaryl, wherein the optional substituents of the optionally substituted substituents are selected from one or more of the group consisting of halogen, —CN, C$_1$–C$_3$-alkyl, C$_1$–C$_3$-alkoxy and CF$_3$;

R$^{16}$ is H, C$_1$–C$_6$-alkyl, which is optionally substituted by phenyl, phenyl, indanyl or heteroaryl, wherein each phenyl, indanyl, and heteroaryl is optionally substituted one or more times by halogen, —CN, C$_1$–C$_3$-alkyl, C$_1$–C$_3$-alkoxy or CF$_3$;

R$^{17}$ is H or C$_1$–C$_6$-alkyl;

R$^{20}$ is C$_1$–C$_{10}$-alkyl, which is optionally substituted one or more times by F, OH, C$_1$–C$_8$-alkoxy, aryloxy, C$_1$–C$_8$-alkylmercapto, C$_1$–C$_8$-alkylamino, or di(C$_1$–C$_8$-alkyl)amino, CF$_3$, optionally substituted phenyl or optionally substituted heteroaryl, wherein the optional substituents of the optionally substituted phenyl and heteroaryl are selected from one or more of the group consisting of halogen, —CN, C$_1$–C$_3$-alkyl, C$_1$–C$_3$-alkoxy and CF$_3$;

R$^{21}$ is H,

C$_1$–C$_{10}$-alkyl, which is optionally substituted one or more times by F, C$_1$–C$_8$-alkoxy or di(C$_1$–C$_8$-alkyl)amino, aryl-(C$_1$–C$_4$-alkyl)- or heteroaryl-(C$_1$–C$_4$-alkyl)-, wherein each of the aryl-(C$_1$–C$_4$-alkyl)- or heteroaryl-(C$_1$–C$_4$-alkyl)- is optionally substituted one or more times by halogen, C$_1$–C$_4$-alkyl, C$_1$–C$_4$-alkoxy or di(C$_1$–C$_6$-alkyl)amino;

R$^{22}$ is H, C$_1$–C$_{10}$-alkyl, which is optionally substituted one or more times by F, C$_1$–C$_8$-alkoxy, di(C$_1$–C$_8$-alkyl)amino or phenyl, phenyl, indanyl or heteroaryl, wherein each phenyl, indanyl and heteroaryl is optionally substituted one or more times by halogen, —CN, C$_1$–C$_3$-alkyl, C$_1$–C$_3$-alkoxy or CF$_3$;

R$^{23}$ is H or C$_1$–C$_{10}$-alkyl;

R$^{24}$ is H, C$_1$–C$_{10}$-alkyl, which is optionally substituted one or more times by F, C$_1$–C$_8$-alkoxy, di(C$_1$–C$_8$-alkyl)amino or phenyl, phenyl, indanyl or heteroaryl, wherein each phenyl, indanyl and heteroaryl is optionally substituted one or more times by halogen, —CN, C$_1$–C$_3$-alkyl, C$_1$–C$_3$-alkoxy or CF$_3$;

R$^{25}$ is H or C$_1$–C$_{10}$-alkyl;

R$^{26}$ is C$_1$–C$_{10}$-alkyl, which is optionally substituted one or more times by F, OH, C$_1$–C$_8$-alkoxy, aryloxy, C$_1$–C$_8$-alkylmercapto, C$_1$–C$_8$-alkylamino, or di(C$_1$–C$_8$-alkyl)amino,

CF$_3$, optionally substituted phenyl or optionally substituted heteroaryl, wherein the optional substituents of the optionally substituted phenyl and heteroaryl are selected from one or more of the group consisting of halogen, —CN, C$_1$–C$_3$-alkyl, C$_1$–C$_3$-alkoxy and CF$_3$;

R$^{27}$ is C$_1$–C$_{10}$-alkyl, which is optionally substituted one or more times by F, OH, C$_1$–C$_8$-alkoxy, aryloxy, C$_1$–C$_8$-alkylmercapto, C$_1$–C$_8$-alkylamino, or di(C$_1$–C$_8$-alkyl)amino,

CF$_3$, optionally substituted phenyl or optionally substituted heteroaryl, wherein the optional substituents of the optionally substituted phenyl and heteroaryl are selected from one or more of the group consisting of halogen, —CN, C$_1$–C$_3$-alkyl, C$_1$–C$_3$-alkoxy and CF$_3$;

wherein heteroaryl is a residue of a 5-membered to 10-membered, aromatic, monocyclic or bicyclic heterocycle containing one or more heteroatoms selected from the group consisting of N, O and S;

wherein aryl is phenyl, naphth-1-yl or naphth-2-yl;

m is 0, 1 or 2; and n is 1, or 3;

or a stereoisomer or a mixture of stereoisomers in any ratio of the compound, or a pharmaceutically acceptable salt of the compound, stereoisomer or mixture of stereoisomers of the compound.

2. The compound according to claim 1 wherein n is 1.

3. The compound according to claim 1 wherein n is 3.

4. The compound according to claim 1 wherein $R^2$ is oxazolyl, thiazolyl or pyrrolyl, each of which is optionally substituted one or more times by F, Cl, Br, $C_1$–$C_3$-alkyl, $C_1$–$C_3$-alkoxymethyl, 2-amino-3,3,3-trifluoropropyl-, $CF_3$, $C_3$–$C_5$-alkandiyl, phenyl, heteroaryl, benzyl, heteroaryl-methyl-, OH, $C_1$–$C_3$-alkoxy, phenoxy, trifluoromethoxy, 2,2,2-trifluoroethoxy, ($C_1$–$C_4$-alkyl)-COO, $C_1$–$C_3$-alkylmercapto, phenylmercapto, $C_1$–$C_3$-alkylsulfonyl, phenylsulfonyl, $NH_2$, $C_1$–$C_4$-alkylamino, di($C_1$–$C_4$-alkyl)amino, ($C_1$–$C_3$-alkyl)-CONH—, ($C_1$–$C_3$-alkyl)-$SO_2$NH—, ($C_1$–$C_3$-alkyl)-CO—, phenyl-CO—, —$OCH_2$O—, —$OCF_2$O—, —$CH_2CH_2$O—, COO($C_1$–$C_4$-alkyl), —$CONH_2$, —CONH($C_1$–$C_4$-alkyl), —CON(di($C_1$–$C_4$-alkyl)), —CN, —$SO_2NH_2$, —$SO_2$NH($C_1$–$C_4$-alkyl), —$SO_2$N(di($C_1$–$C_4$-alkyl)), pyrrolidinyl, piperidinyl, morpholinyl or thiomorpholinyl, and wherein for each oxazolyl, thiazolyl or pyrrolyl as $R^2$ bearing an heteroaryl, phenyl, heteroaryl-containing or phenyl-containing group as an optional substituent, that each heteroaryl, phenyl, heteroaryl-containing and phenyl-containing group is optionally substituted one or more times by halogen, —CN, $C_1$–$C_3$-alkyl, OH, $C_1$–$C_3$-alkoxy or $CF_3$.

5. A pharmaceutical composition, comprising a pharmaceutically effective amount of the compound according to claim 1 or a stereoisomer or a mixture of stereoisomers in any ratio of the compound, or a pharmaceutically acceptable salt of the compound, stereoisomer or mixture of stereoisomers of the compound, and a pharmaceutically acceptable carrier.

6. A method of treating stable or unstable angina pectoris, coronary heart disease, Prinzmetal angina, acute coronary syndrome, heart failure, myocardial infarction, stroke, thrombosis, peripheral artery occlusive disease, endothelial dysfunction, atherosclerosis, essential hypertension, pulmonary hypertension, secondary hypertension, renovascular hypertension, or ventricular arrhythmia, in a patient in need thereof, wherein said method is mediated by the expression of endothelial nitric oxide synthase, comprising administering to such patient a pharmaceutically effective amount of the compound according to claim 1 or a stereoisomer or a mixture of stereoisomers in any ratio of the compound, or a pharmaceutically acceptable salt of the compound, stereoisomer or mixture of stereoisomers of the compound.

7. The compound according to claim 1 wherein $R^1$ is optionally substituted phenyl.

* * * * *